US012734263B2

(12) United States Patent
Kim et al.

(10) Patent No.: US 12,734,263 B2
(45) Date of Patent: Sep. 15, 2026

(54) PORTABLE IPL STERILIZER AND IPL TOILET BOWL STERILIZER

(71) Applicant: IUCF-HYU (INDUSTRY-UNIVERSITY COOPERATION FOUNDATION HANYANG UNIVERSITY), Seoul (KR)

(72) Inventors: Young Beom Kim, Seoul (KR); Yong Hyun Lim, Seoul (KR); Sung Keun Park, Seoul (KR); Han Sam Lee, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 900 days.

(21) Appl. No.: 18/061,292

(22) Filed: Dec. 2, 2022

(65) Prior Publication Data

US 2023/0100079 A1 Mar. 30, 2023

Related U.S. Application Data

(63) Continuation of application No. PCT/KR2021/006817, filed on Jun. 1, 2021.

(30) Foreign Application Priority Data

Jun. 2, 2020 (KR) ........................ 10-2020-0066322
Jun. 2, 2020 (KR) ........................ 10-2020-0066323

(51) Int. Cl.
*A61L 2/10* (2026.01)
*A61L 2/22* (2006.01)
(Continued)

(52) U.S. Cl.
CPC .................. *A61L 2/10* (2013.01); *A61L 2/22* (2013.01); *A61L 2/24* (2013.01); *A61L 2/26* (2013.01);
(Continued)

(58) Field of Classification Search
CPC ..... A61L 2/10; A61L 2/22; A61L 2/24; A61L 2/26; H05B 47/17
See application file for complete search history.

(56) References Cited

U.S. PATENT DOCUMENTS

2005/0166863 A1 8/2005 Park et al.
2018/0339075 A1* 11/2018 Kennedy .................. A61L 2/24

FOREIGN PATENT DOCUMENTS

CN 103976685 B * 6/2016
JP 2009-261755 A 11/2009
(Continued)

OTHER PUBLICATIONS

English translation of JP-2017008607-A (Year: 2017).*
English translation of CN-103976685-B (Year: 2016).*
English translation of KR-20110131898-A (Year: 2011).*
International Search Report for PCT/KR2021/006817 dated Sep. 6, 2021.

*Primary Examiner* — Sean E Conley
(74) *Attorney, Agent, or Firm* — Sughrue Mion, PLLC

(57) ABSTRACT

Provided is a portable IPL sterilizer comprising: a body partitioned into a central region and a peripheral region surrounding at least a portion of the central region; a xenon lamp light source for sterilization provided in the central region of the body; and a light-shielding comb part provided in the peripheral region of the body.

6 Claims, 34 Drawing Sheets

(51) Int. Cl.

| | |
|---|---|
| ***A61L 2/24*** | (2006.01) |
| ***A61L 2/26*** | (2006.01) |
| ***E03D 9/00*** | (2006.01) |
| ***H01J 61/02*** | (2006.01) |
| ***H01J 61/16*** | (2006.01) |
| ***H05B 41/36*** | (2006.01) |
| ***H05B 47/17*** | (2020.01) |

(52) U.S. Cl.

CPC ............ *E03D 9/005* (2013.01); *H01J 61/025* (2013.01); *H01J 61/16* (2013.01); *H05B 41/36* (2013.01); *H05B 47/17* (2020.01); *A61L 2202/11* (2013.01); *A61L 2202/14* (2013.01); *A61L 2202/15* (2013.01); *A61L 2202/16* (2013.01)

(56) References Cited

FOREIGN PATENT DOCUMENTS

| | | | | | |
|---|---|---|---|---|---|
| JP | 2017-8606 | A | | 1/2017 | |
| JP | 2017008607 | A | * | 1/2017 | |
| JP | 10-2017-0139854 | A | | 12/2017 | |
| KR | 10-2010-0002714 | A | | 1/2010 | |
| KR | 20110131898 | A | * | 12/2011 | .............. A61L 2/10 |
| KR | 10-1254769 | B1 | | 4/2013 | |
| KR | 10-1958946 | B1 | | 3/2019 | |
| KR | 10-2048907 | B1 | | 12/2019 | |
| KR | 10-2071039 | B1 | | 1/2020 | |

* cited by examiner

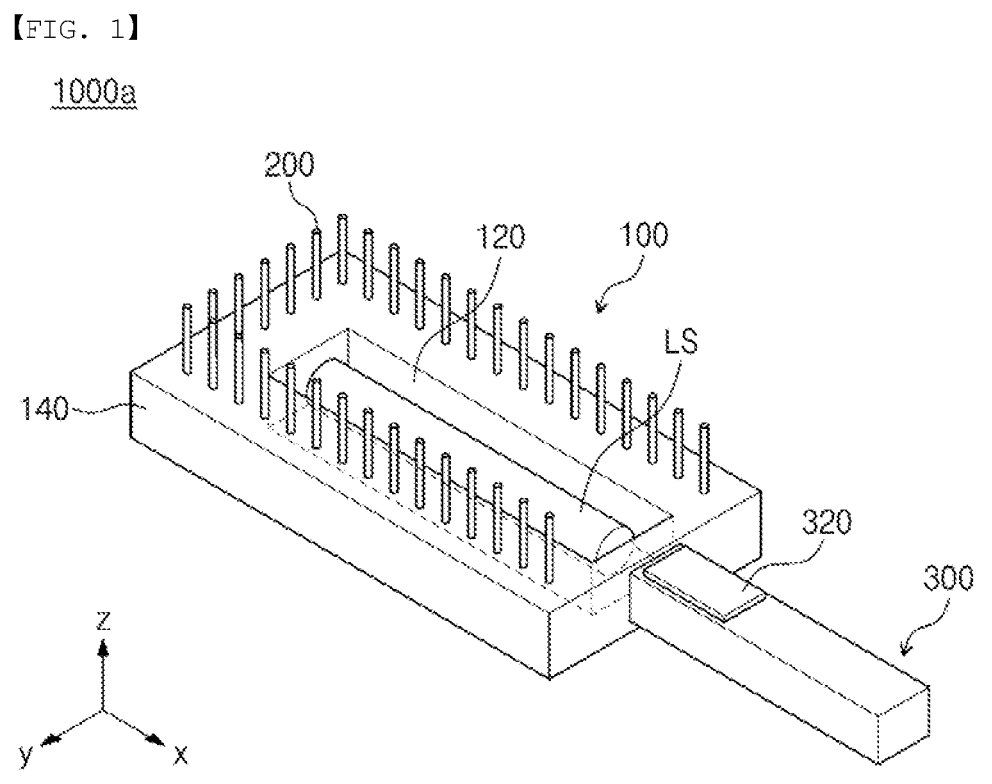

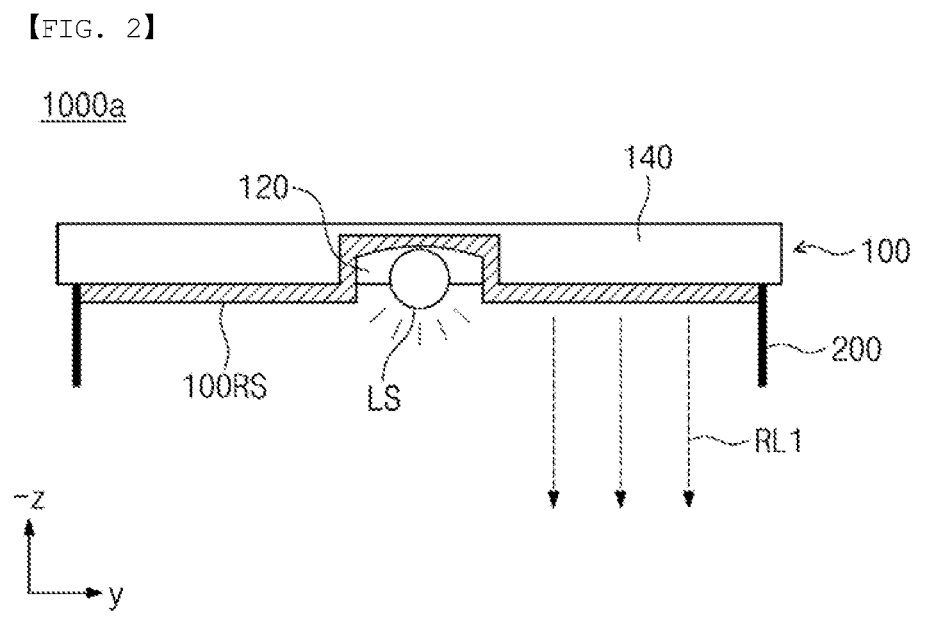

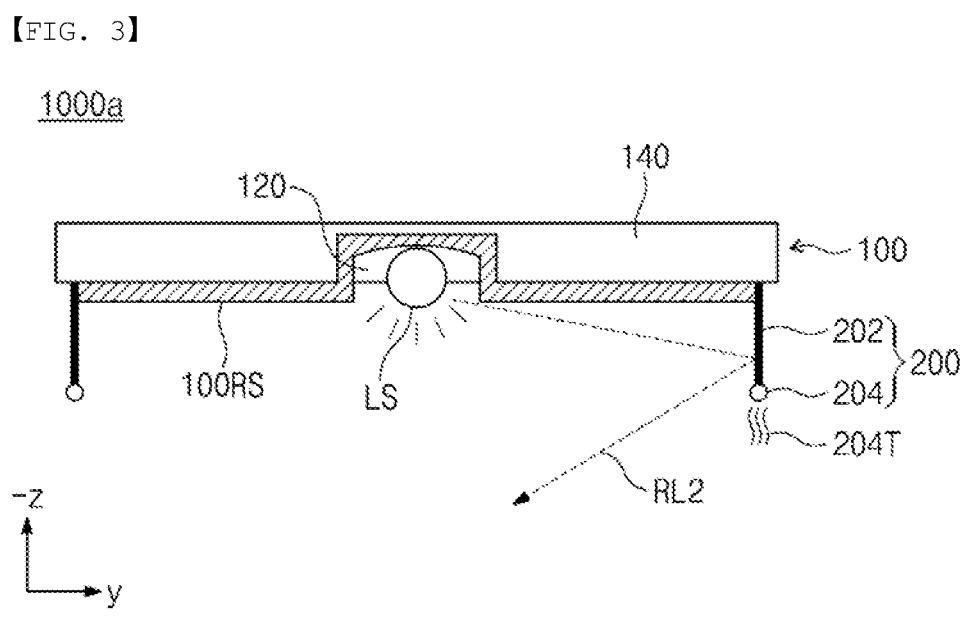

【FIG. 4】
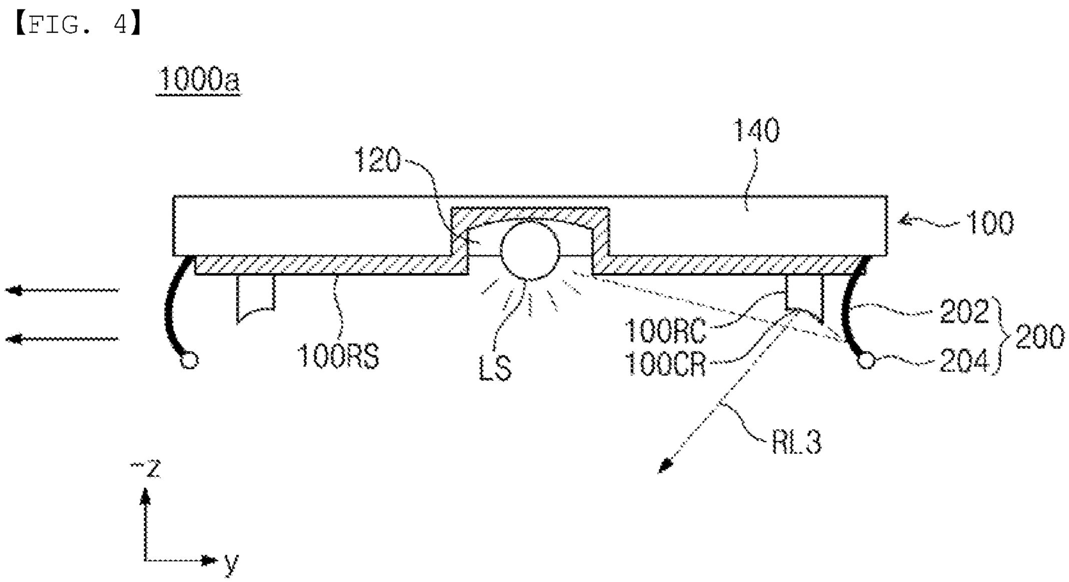

【FIG. 5】
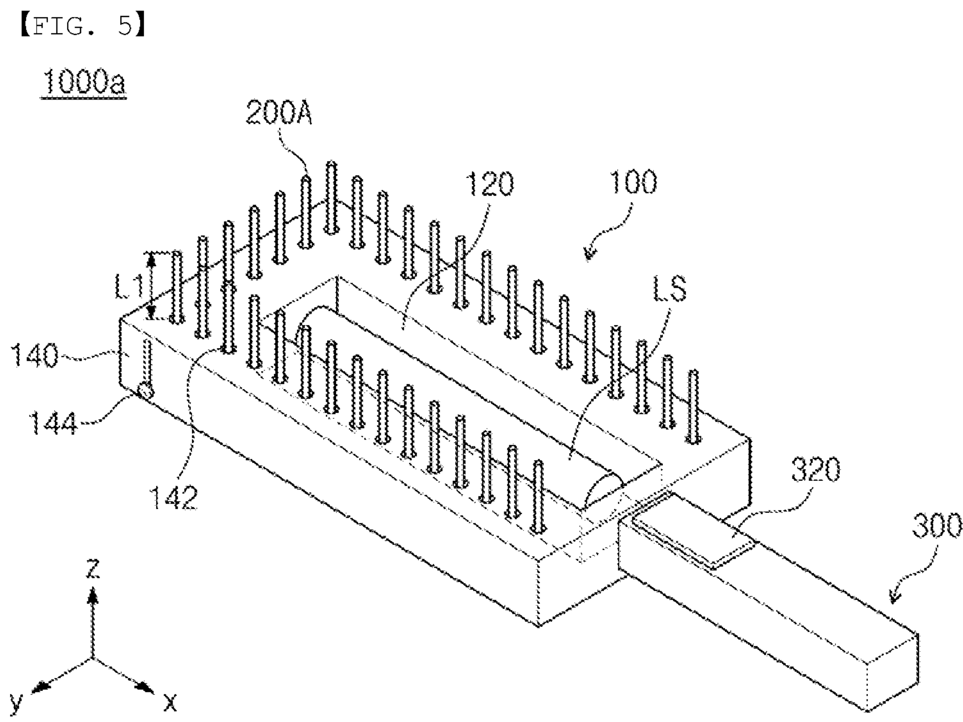

【FIG. 6】
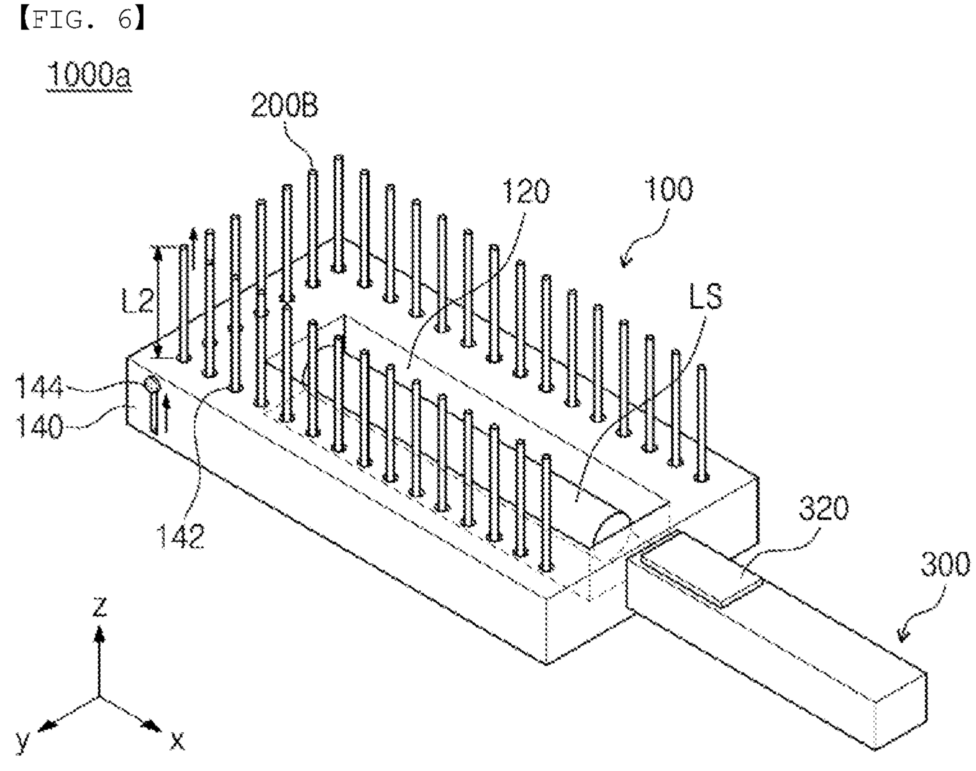

【FIG. 7】
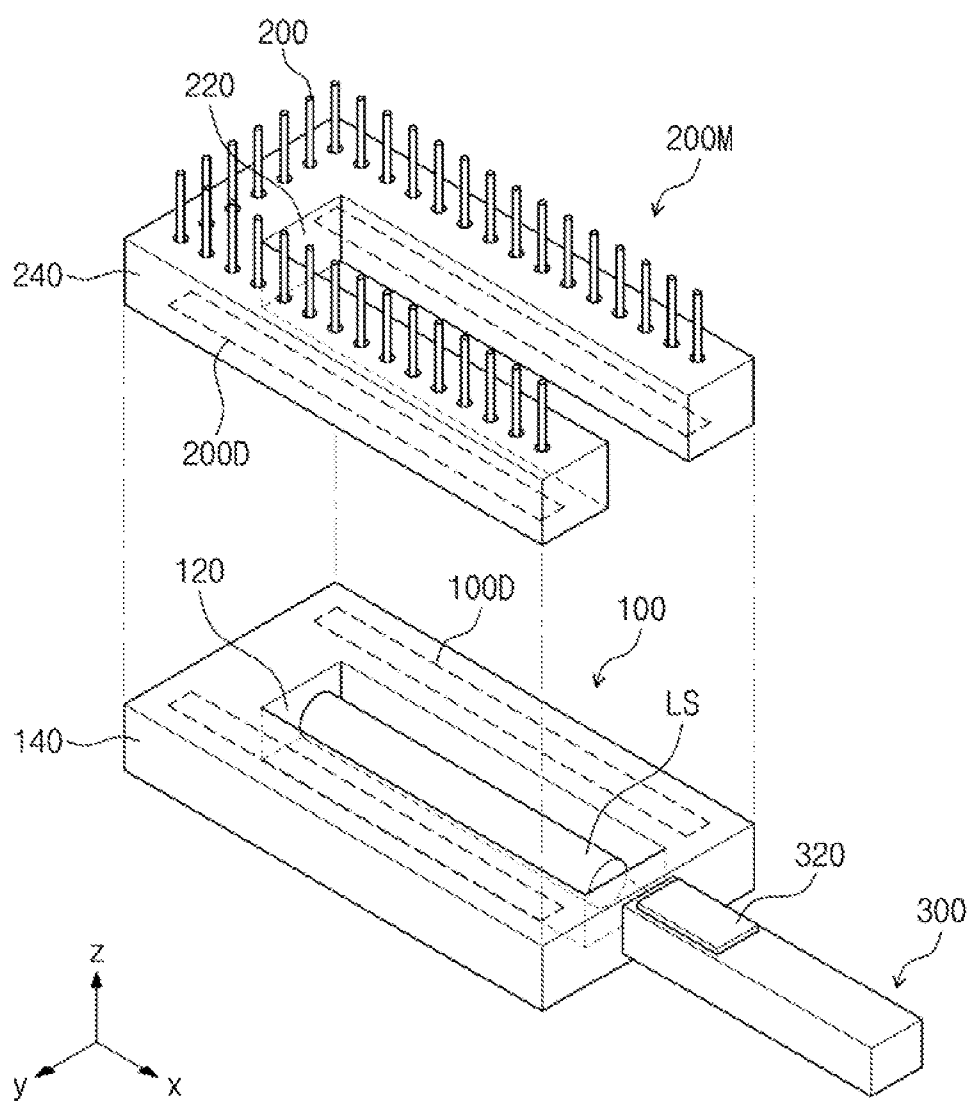

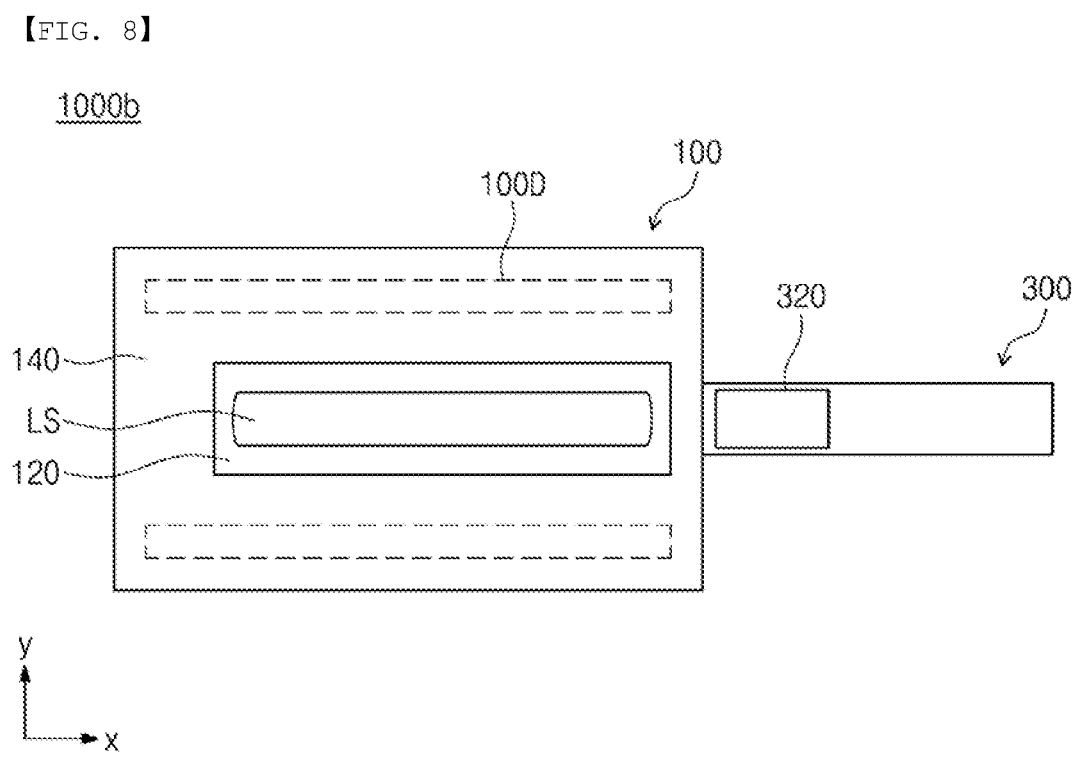

【FIG. 9】
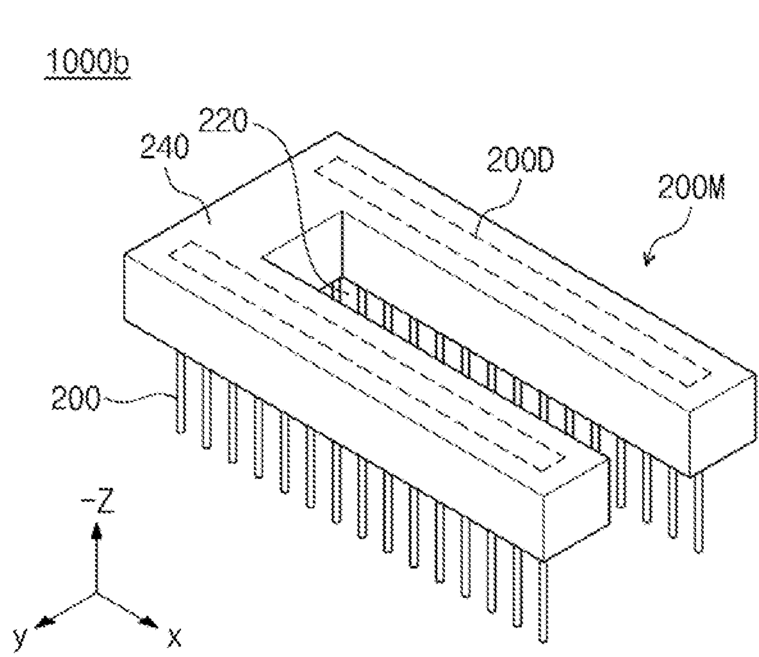

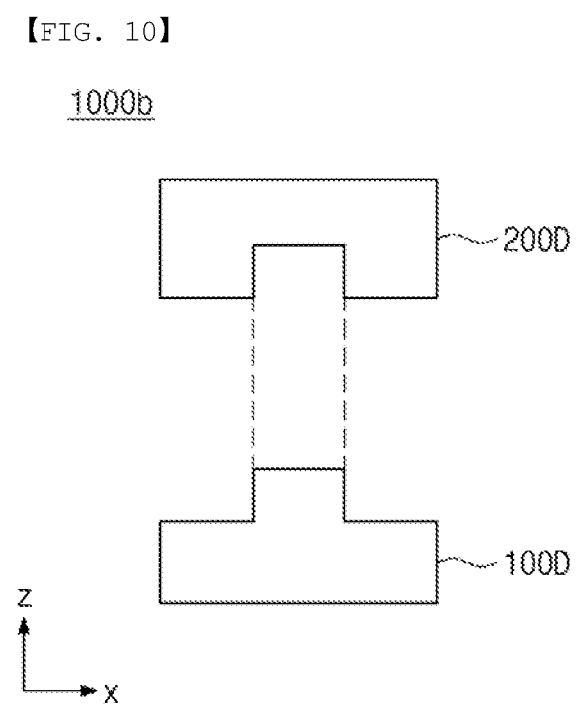

【FIG. 11】
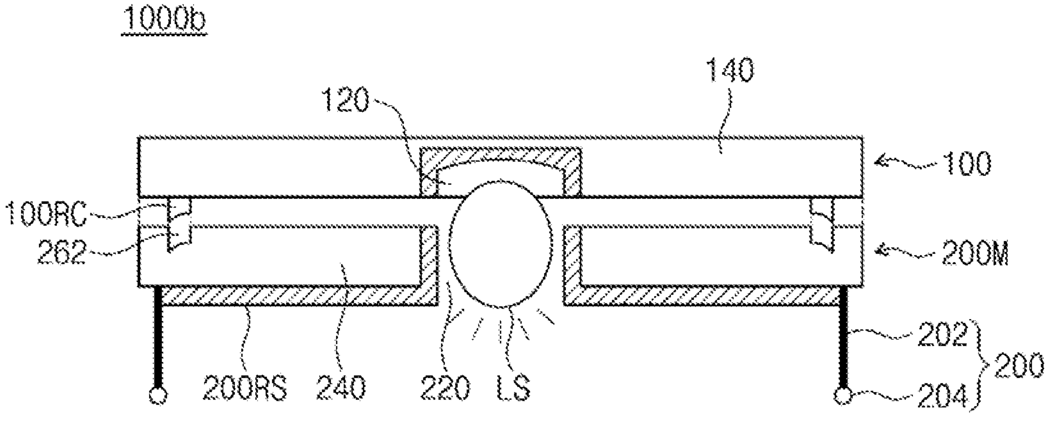
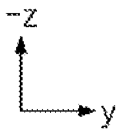

【FIG. 12】
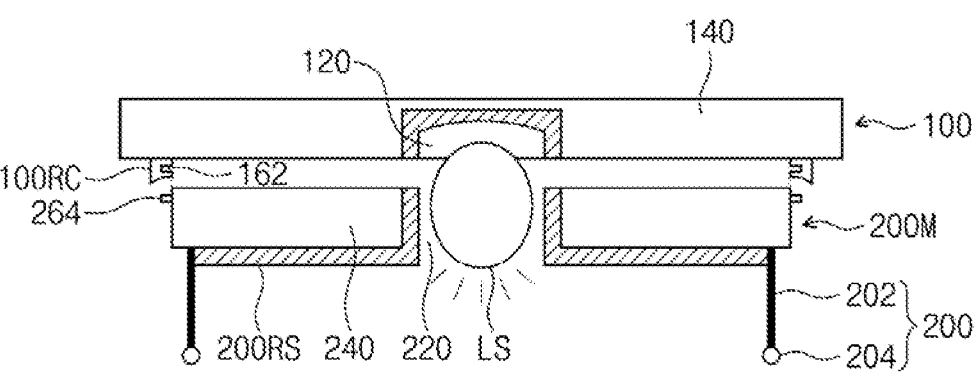
1000b
140
120
100
100RC
162
264
200M
202
200
200RS
240
220
LS
204
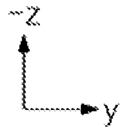
-z
y

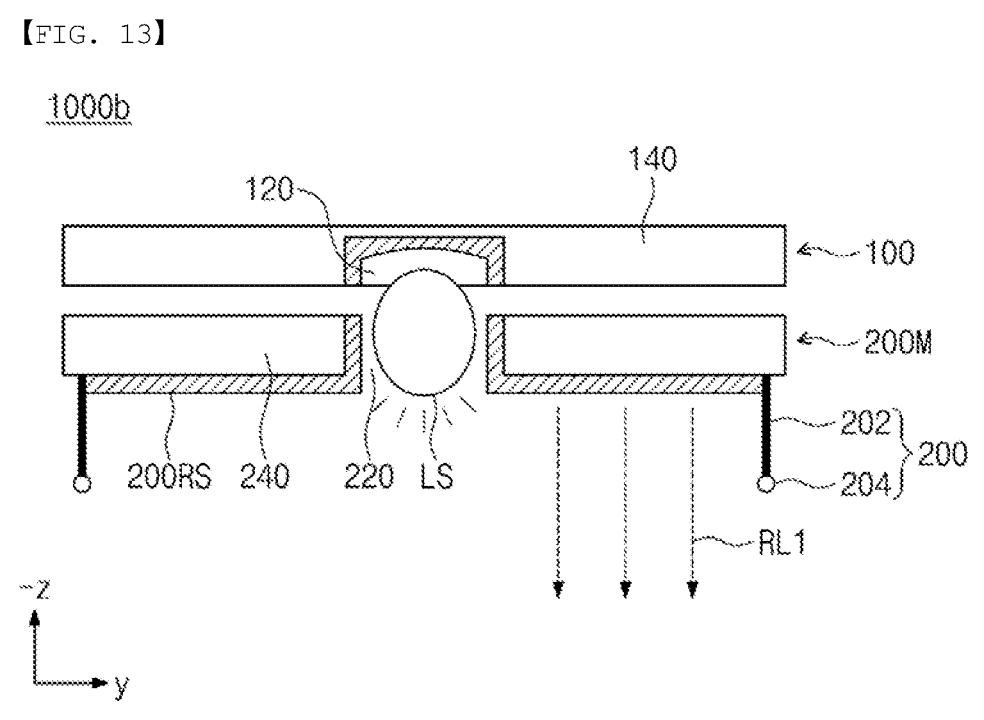

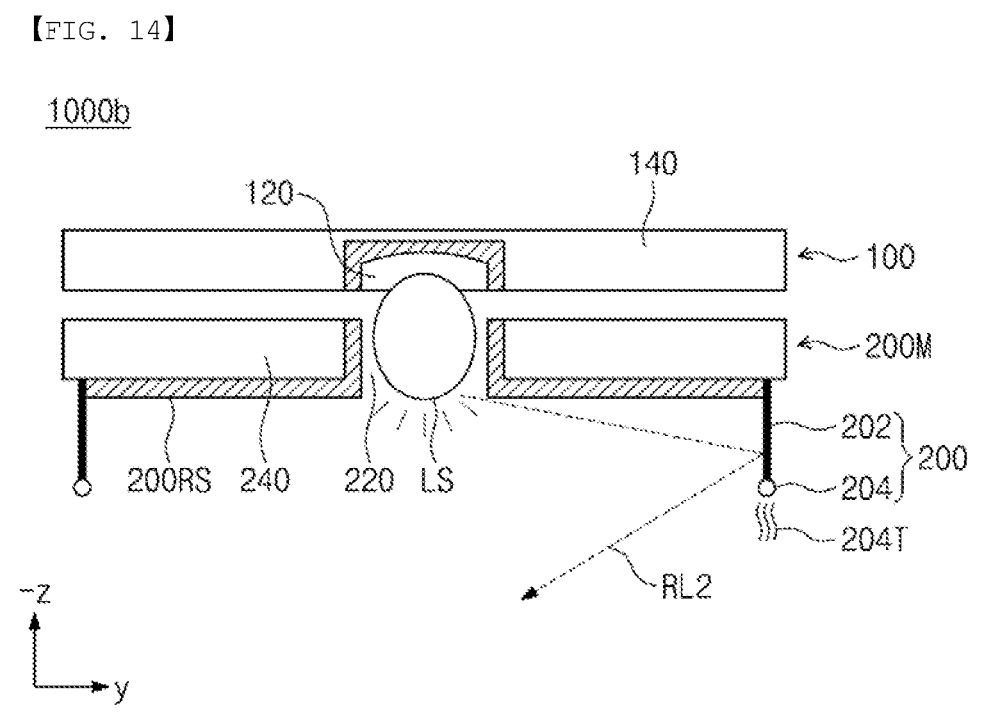

【FIG. 15】
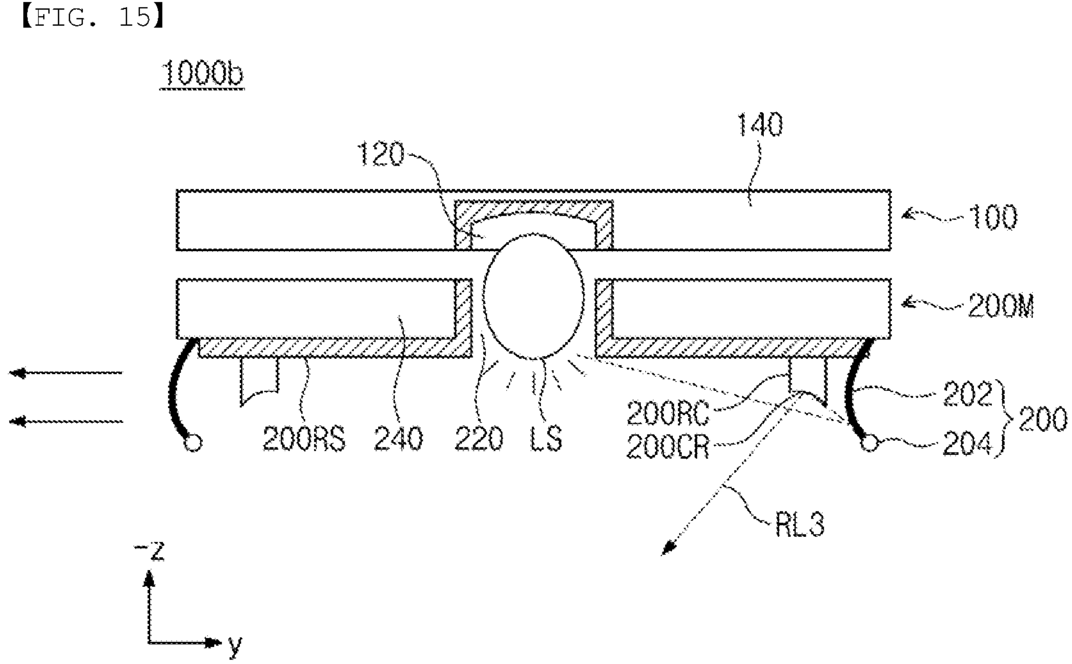

【FIG. 16】
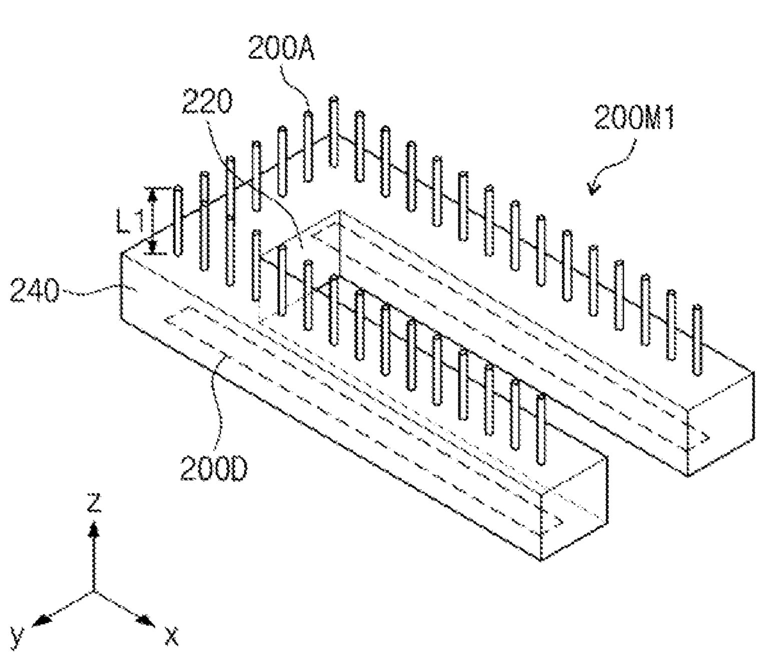

【FIG. 17】
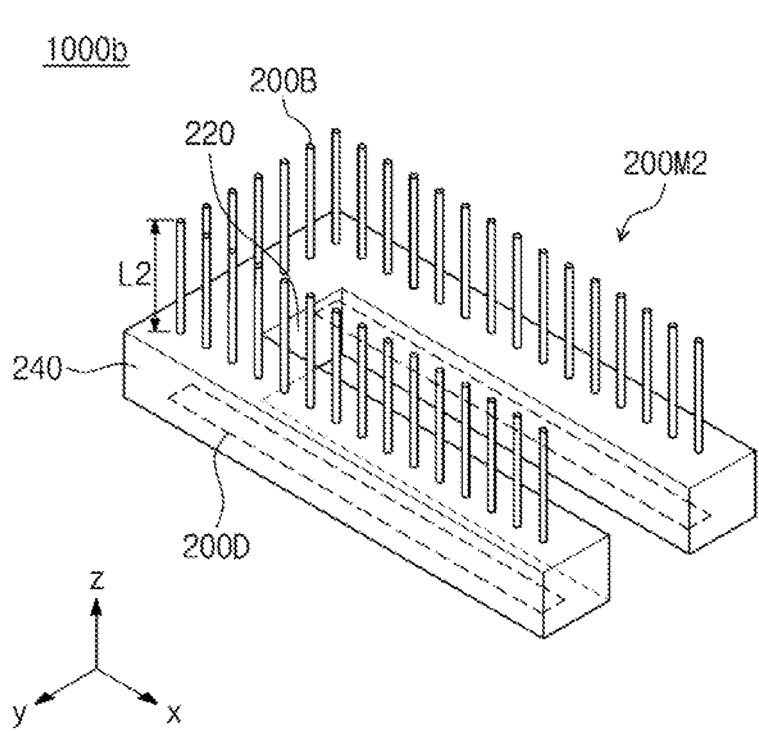

【FIG. 18】
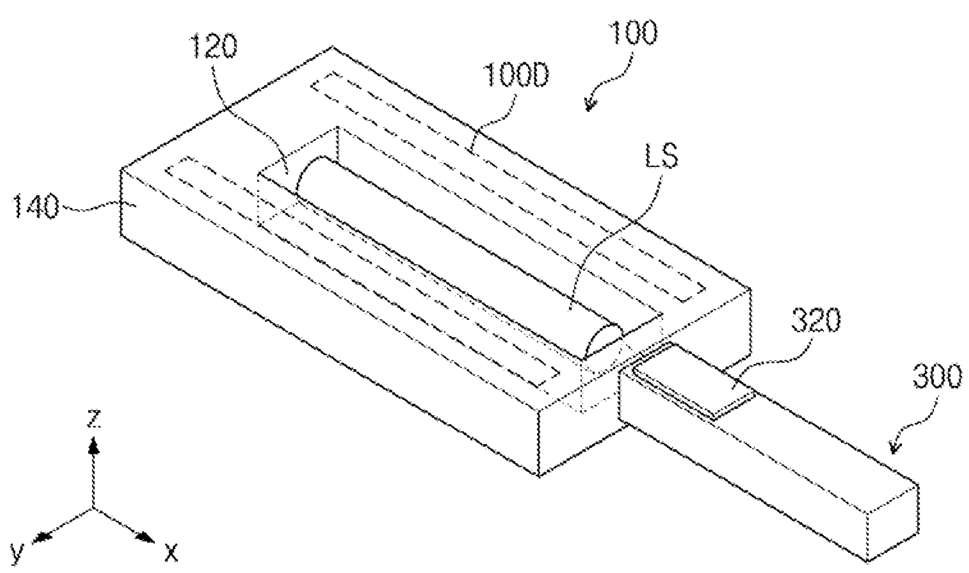

【FIG. 19】
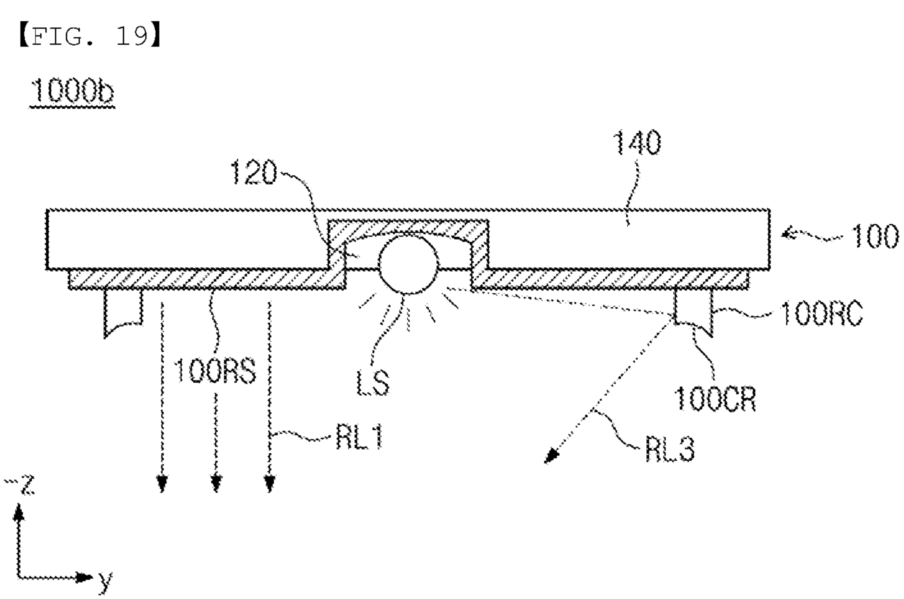

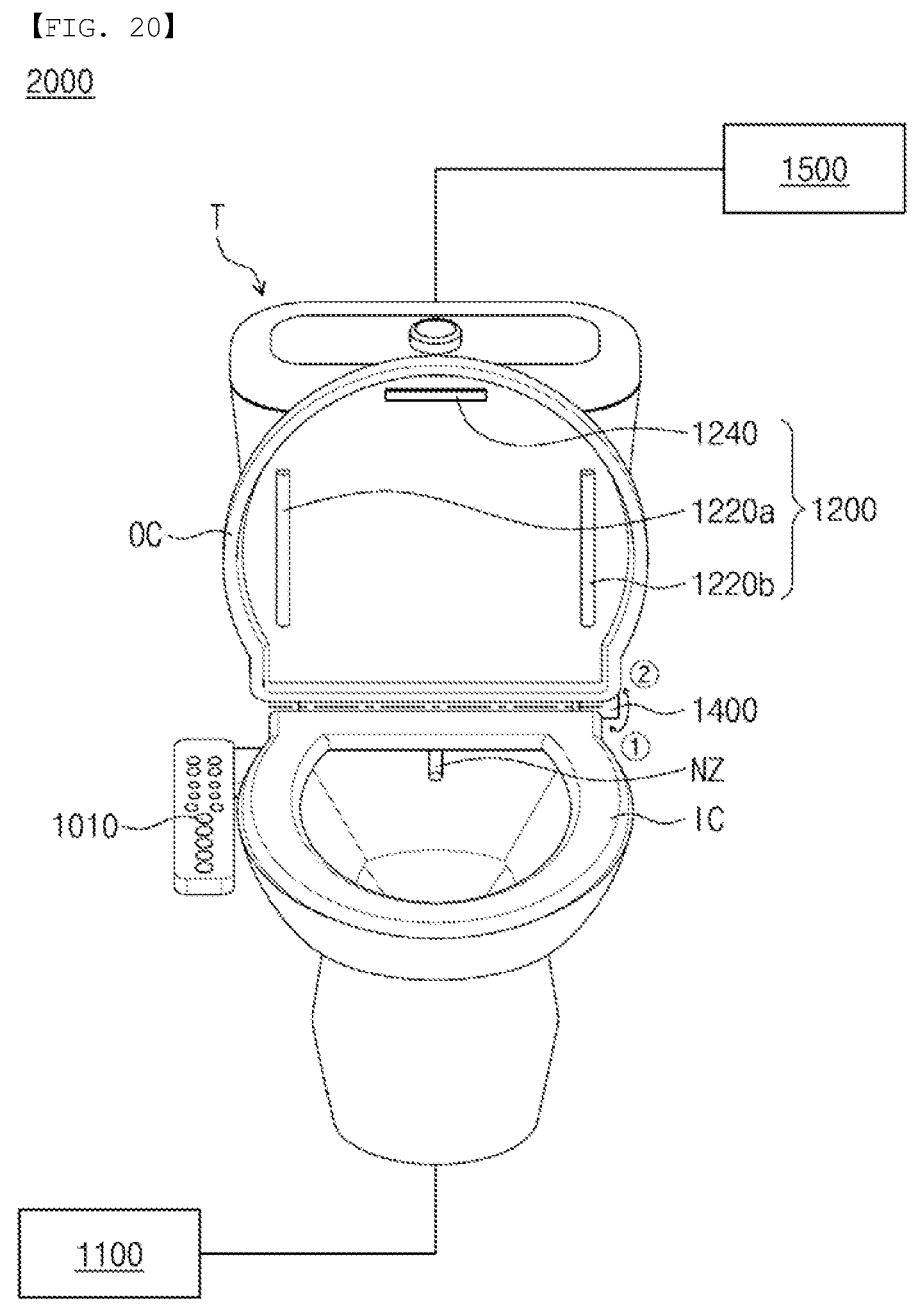

【FIG. 21】
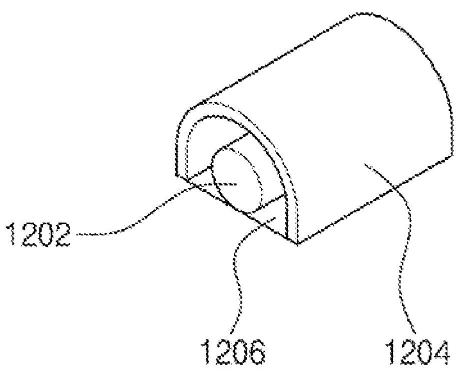

[FIG. 22]
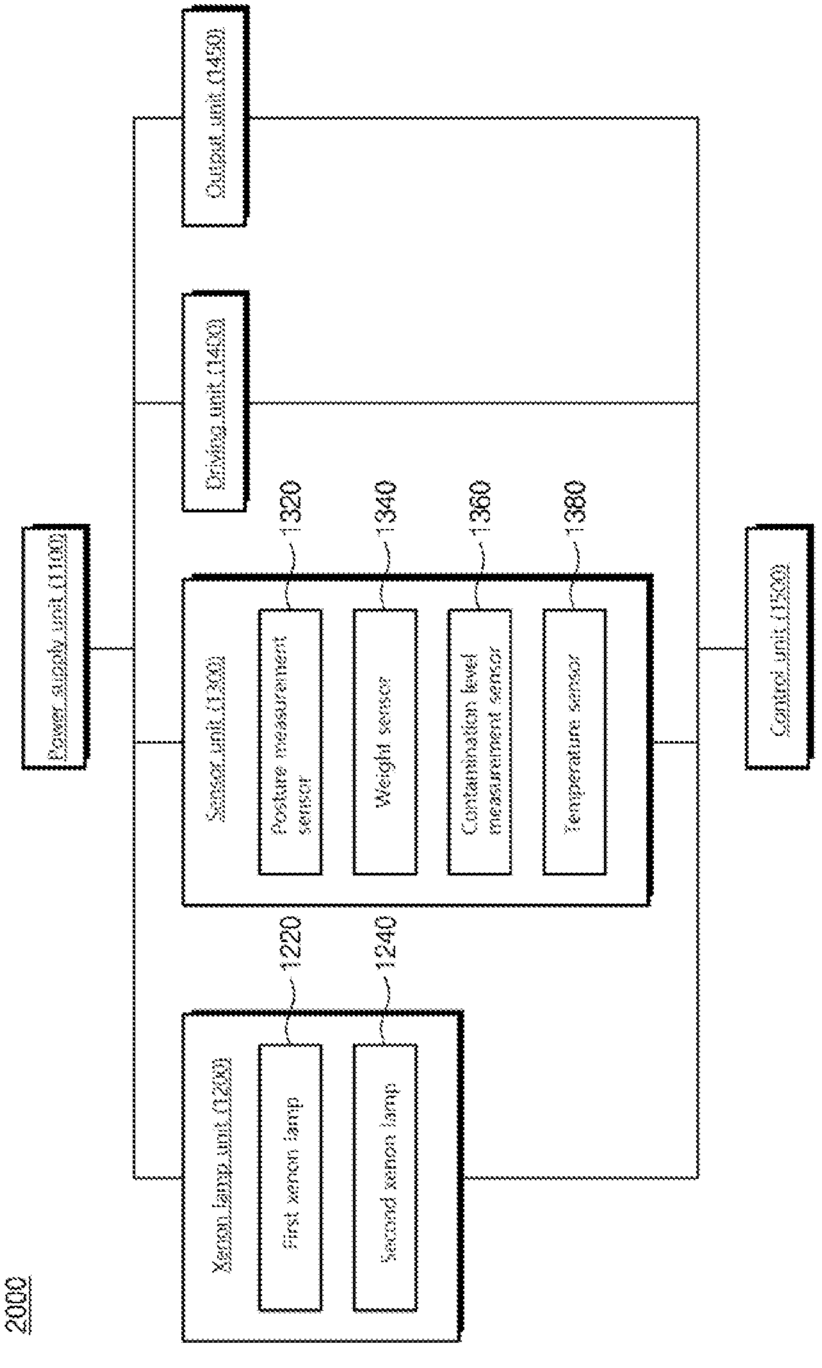

【FIG. 23】
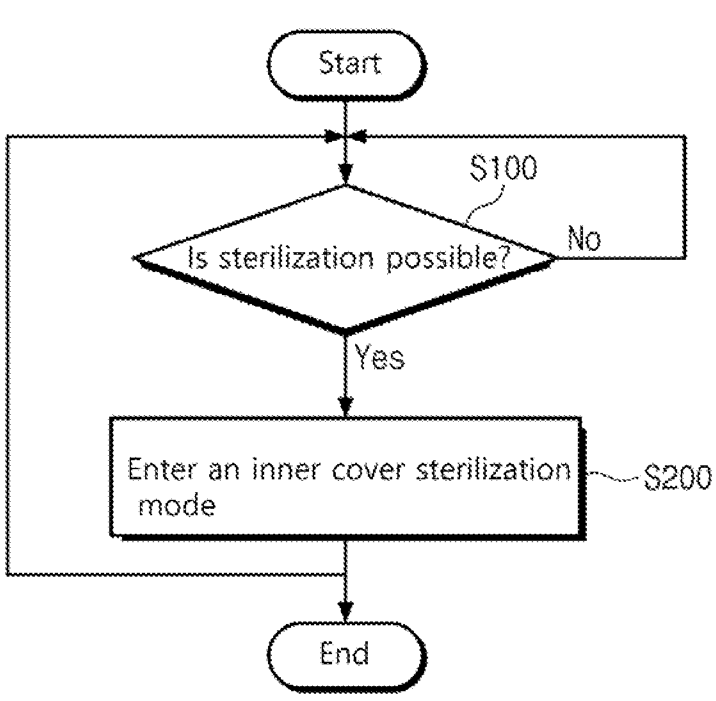

Figure 24:
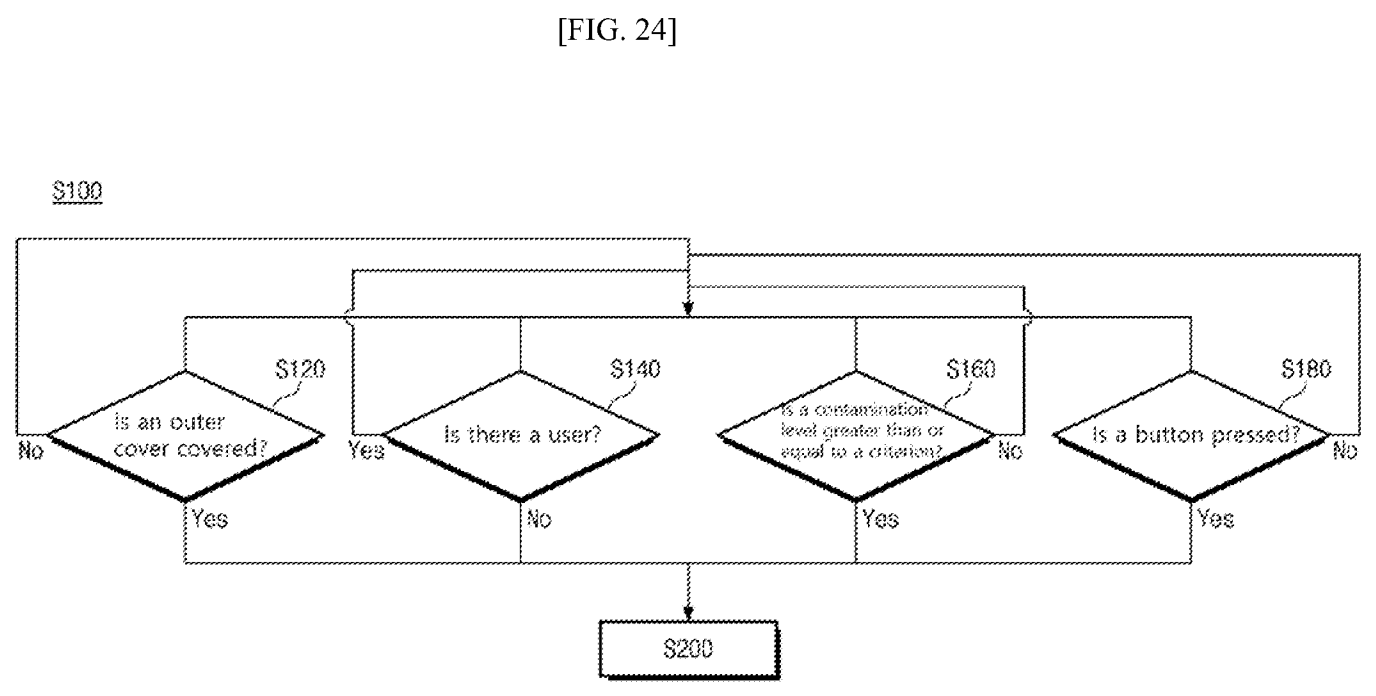

S120
Is an outer cover covered?
Yes
No

S140
Is there a user?
Yes
No

S160
Is a contamination level greater than or equal to a criterion?
Yes
No

S180
Is a button pressed?
Yes
No

S200

【FIG. 25】
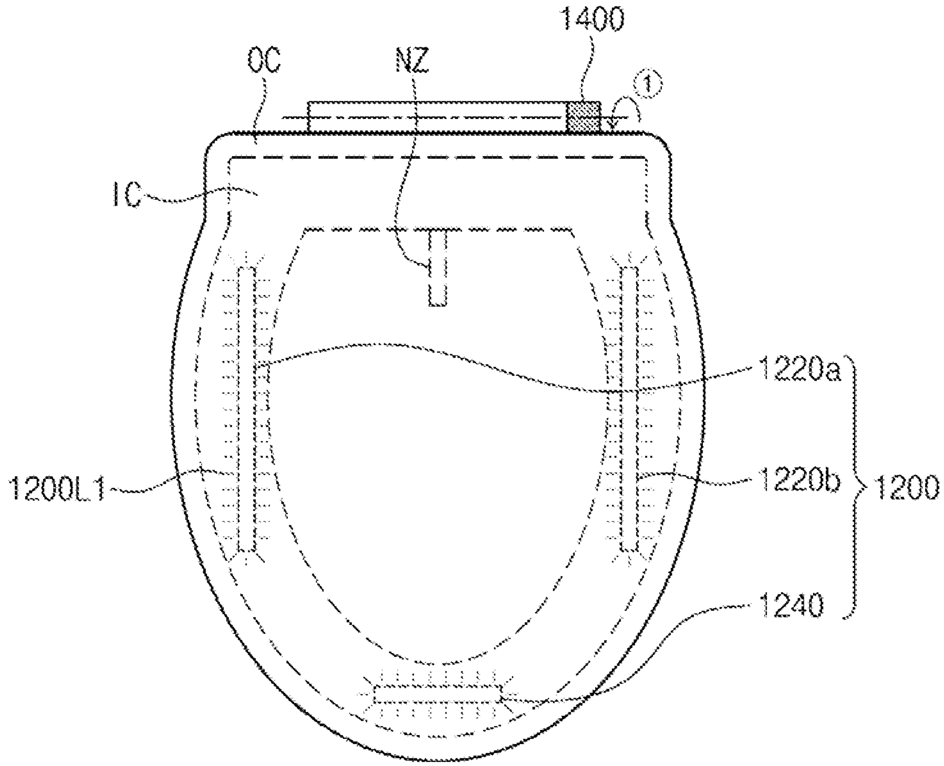

【FIG. 26】
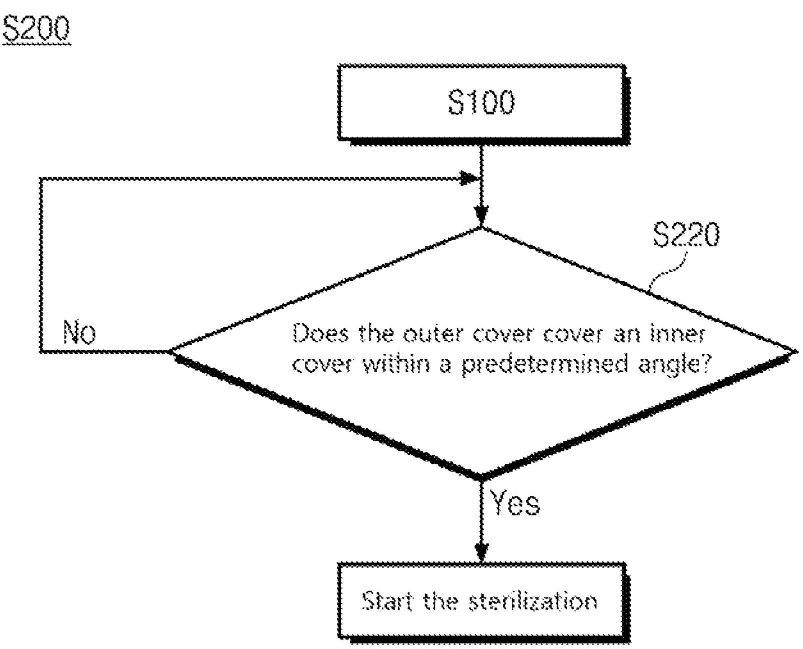

【FIG. 27】
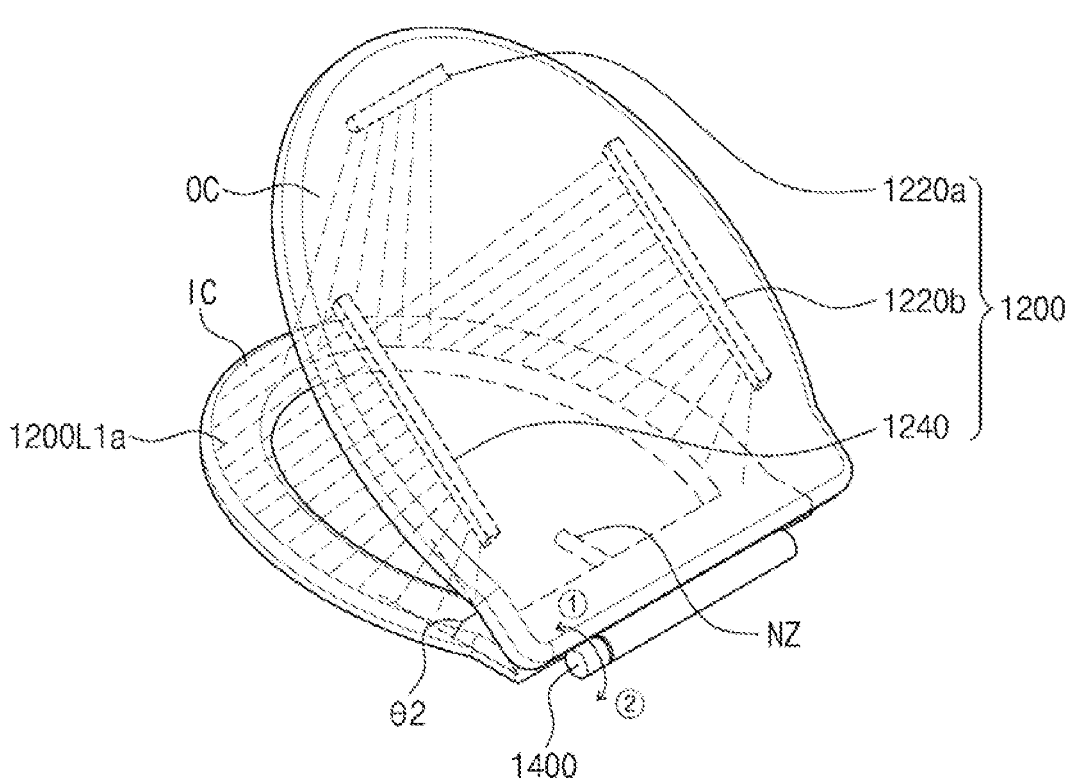

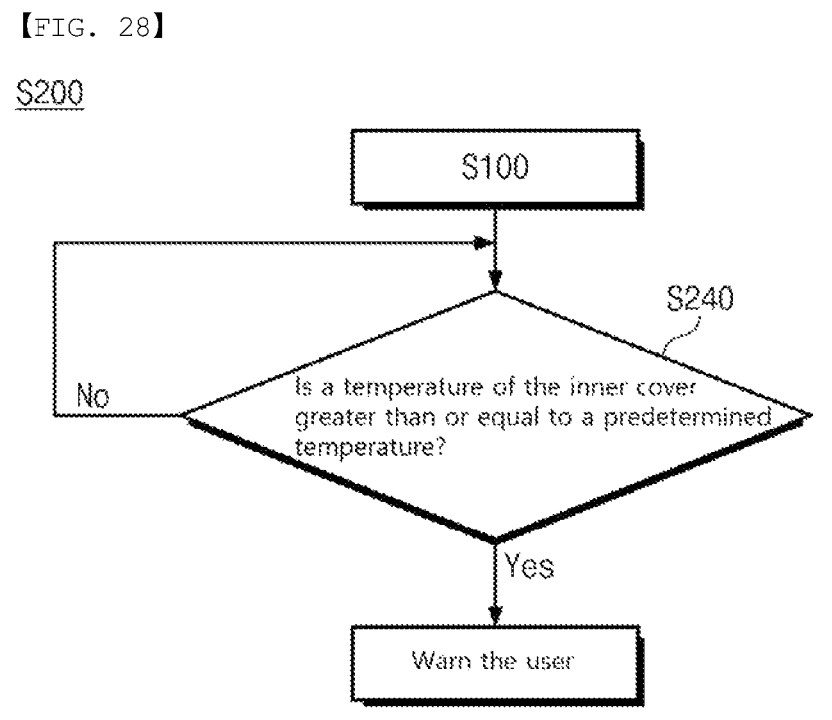

Is a temperature of the inner cover greater than or equal to a predetermined temperature?

No

Yes

Warn the user

【FIG. 29】
2000,S200
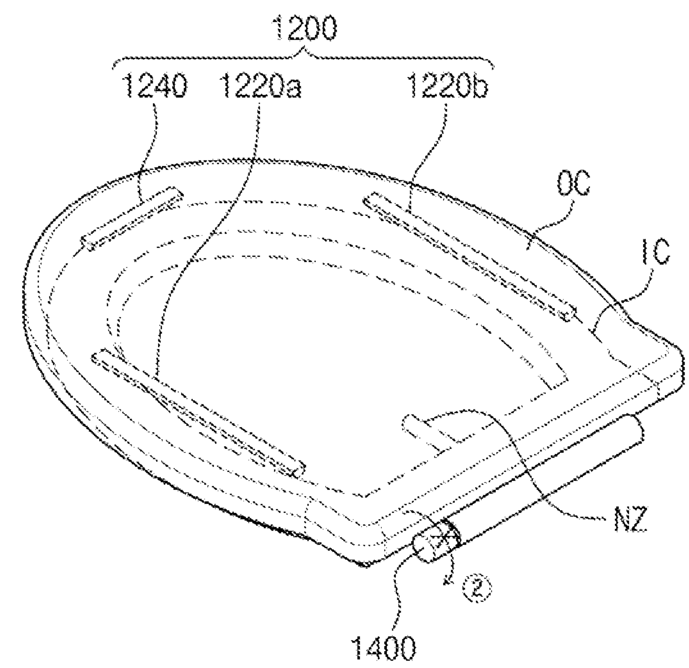
<Locking state>
The temperature of the inner cover is high.
1450

【FIG. 30】
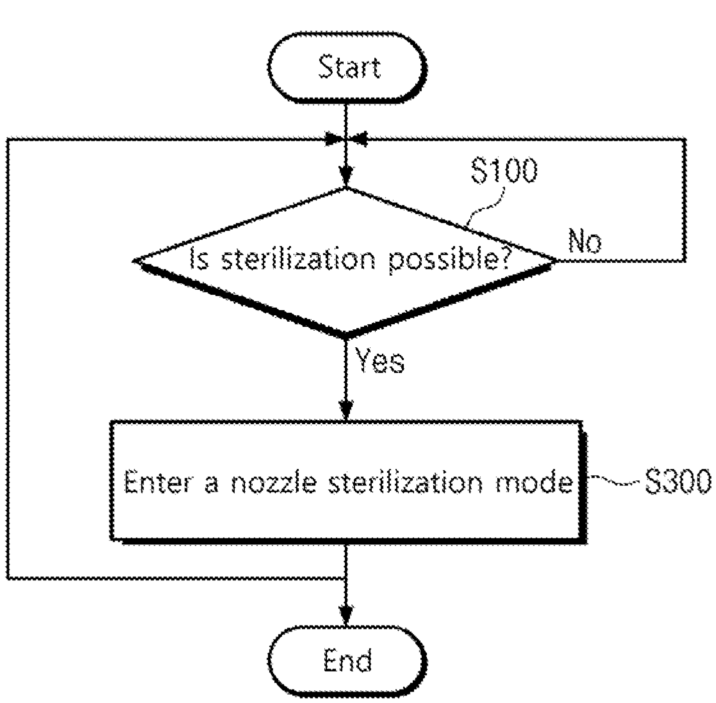

【FIG. 31】
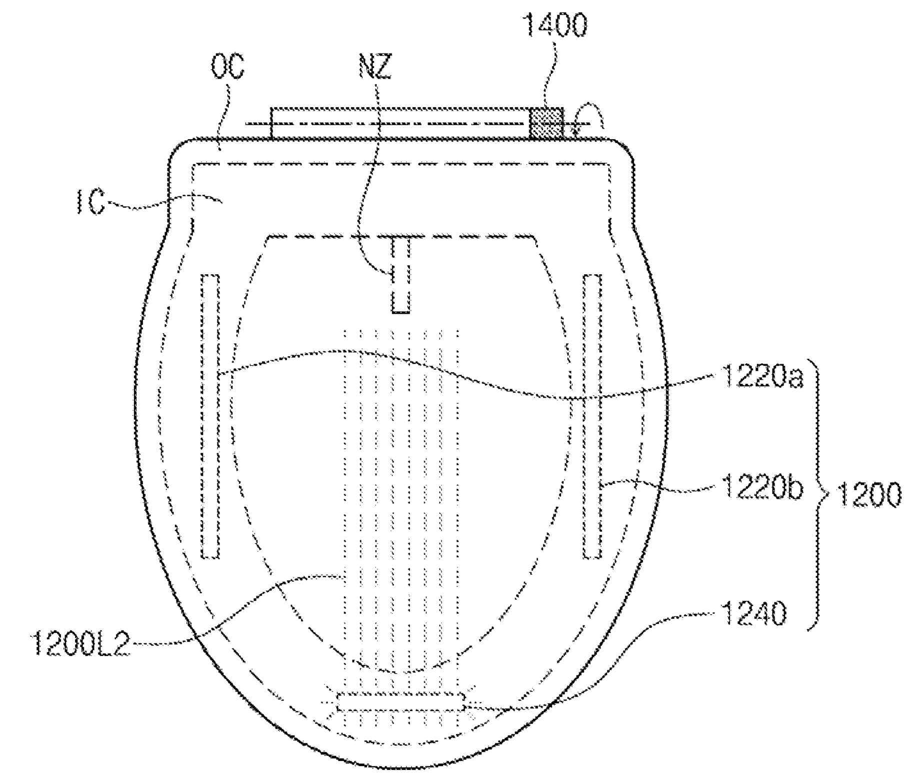

【FIG. 32】
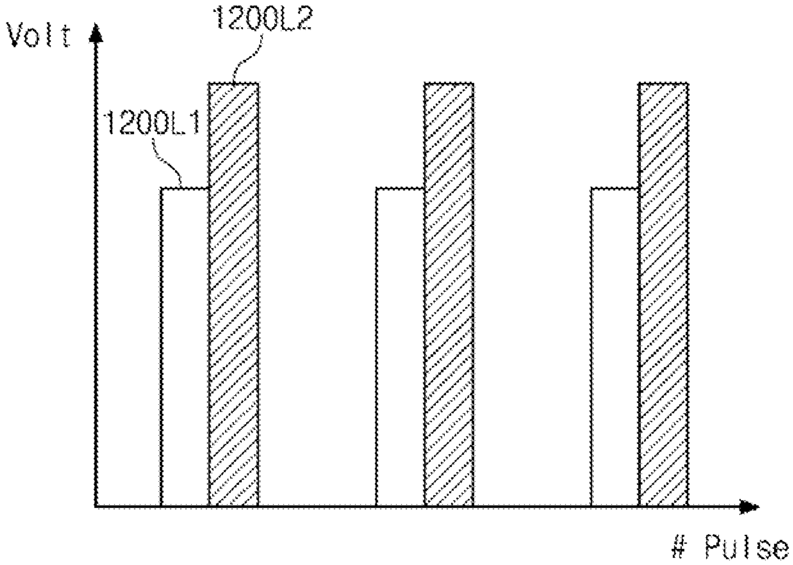

【FIG. 33】
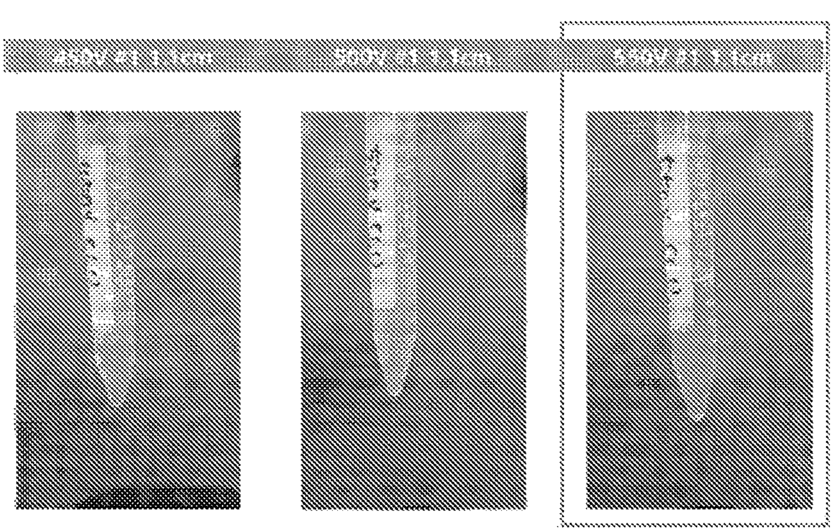

【FIG. 34】
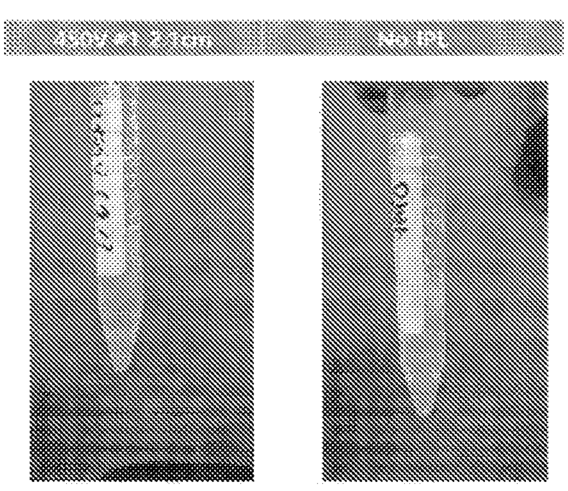

PORTABLE IPL STERILIZER AND IPL TOILET BOWL STERILIZER

CROSS REFERENCE TO RELATED APPLICATIONS

This application is a Continuation of International Application No. PCT/KR2021/006817 filed Jun. 1, 2021, claiming priority based on Korean Patent Application No. 10-2020-0066322 filed Jun. 2, 2020 and Korean Patent Application No. 10-2020-0066323 filed Jun. 2, 2020, the disclosures of which are incorporated herein by reference in their entireties.

TECHNICAL FIELD

The present invention relates to a portable IPL sterilizer and an IPL toilet bowl sterilizer, and more particularly, to a portable IPL sterilizer configured to sterilize a sterilization target by emitting an intense pulsed light (IPL) and an IPL toilet bowl sterilizer configured to sterilize an inner cover of a toilet bowl or a nozzle of a bidet in a non-contact manner within a short time.

BACKGROUND ART

Recently, as the virus problem emerges as a serious problem around the world, interest in sterilization is increasing.

Accordingly, interest in sterilizers for sterilizing a sterilization target is also increasing. Accordingly, according to the related art, a sterilizer for sterilizing a sterilization target by using an ultraviolet light source has been developed.

In this case, the sterilization target may be understood as a concept that includes not only humans and animals, but also specific places, predetermined spaces, and specific objects, such as bathrooms, sink drainage holes, and toys.

However, when an ultraviolet light is used to sterilize the sterilization target, a great amount of time may be required.

Therefore, there is a demand for a more efficient sterilizer.

A toilet bowl cover installed on a toilet bowl may include an inner cover having a region on which a user is seated, and an outer cover configured to rotate relative to the inner cover.

There are various types of pathogenic bacteria on the toilet bowl. Accordingly, there may be various types of pathogenic bacteria on the toilet bowl cover installed on the toilet bowl.

Since the pathogenic bacteria cause various diseases, people avoid making direct contact with the toilet bowl or the toilet bowl cover.

However, since the user has to be seated on the inner cover to use the toilet bowl, it may be difficult to avoid making direct contact with the inner cover.

Accordingly, according to the related art, a method for sterilizing an inner cover by directly applying a sterilization agent has been used. In this case, contact between a person who applies the sterilization agent and the inner cover to which the sterilization agent is applied may be required.

Therefore, people who avoid making direct contact with the toilet bowl or the toilet bowl cover may feel uncomfortable or repulsive due to contact with the toilet bowl or the toilet bowl cover.

Accordingly, according to the related art, a method for sterilizing an inner cover by emitting an ultraviolet light has been studied.

However, when the ultraviolet light is used, a great amount of time may be required.

Therefore, there is a demand for a device capable of sterilizing an inner cover within a short time.

DISCLOSURE

Technical Problem

One technical object of the present invention is to provide a portable IPL sterilizer capable of efficiently sterilizing a sterilization target within a short time.

Another technical object of the present invention is to provide a portable IPL sterilizer in which a light emitted from a light source effectively reaches a sterilization target.

Still another technical object of the present invention is to provide a portable IPL sterilizer capable of performing combing that is optimized for a length of scalp hair or body hair of a sterilization target.

Yet another technical object of the present invention is to provide a portable IPL sterilizer capable of sterilizing not only humans and animals, but also specific places, predetermined spaces, and specific objects.

One technical object of the present invention is to provide an IPL toilet bowl sterilizer capable of sterilizing an inner cover of a toilet bowl or a nozzle of a bidet within a short time.

Another technical object of the present invention is to provide an IPL toilet bowl sterilizer capable of sterilizing an inner cover of a toilet bowl or a nozzle of a bidet in a non-contact manner.

Technical objects of the present invention are not limited to the technical objects described above.

Technical Solution

To achieve the technical objects described above, according to the present invention, there is provided a portable IPL sterilizer.

According to one embodiment, the portable IPL sterilizer includes: a body partitioned into a central region and a peripheral region surrounding at least a portion of the central region; a sterilization xenon lamp light source provided in the central region of the body; and a light-shielding comb part provided in the peripheral region of the body.

According to one embodiment, the portable IPL sterilizer includes: a body partitioned into a central region and a peripheral region surrounding at least a portion of the central region; a sterilization xenon lamp light source provided in the central region of the body; and at least one light-shielding comb module including a light-shielding comb part and detachably attached to the peripheral region of the body.

According to one embodiment, a reflective surface may be formed on one surface of the central or peripheral region of the body or on one surface of the light-shielding comb part, and the reflective surface may be configured to reflect a light emitted from the sterilization xenon lamp light source toward a sterilization target.

According to one embodiment, the light-shielding comb part may include: a comb body part extending from the peripheral region of the body by a predetermined length and configured to reflect a light emitted from the sterilization xenon lamp light source; and a thermochromic discoloration part provided at one end of the comb body part and discolored by the light emitted from the sterilization xenon lamp light source.

According to one embodiment, at least one reflective member protruding by a predetermined length may be formed on one side of the peripheral region of the body or on one side of the light-shielding comb part, and the reflective member may include a curved part configured to reflect the light, which is emitted from the sterilization xenon lamp light source and reflected from the comb body part, toward a sterilization target.

According to one embodiment, the body may include an accommodation groove through which at least a portion of the light-shielding comb part is accommodated in the body in a longitudinal direction of the light-shielding comb part, and the portable IPL sterilizer may further include a comb length adjustment unit configured to adjust an accommodation length of the light-shielding comb part accommodated in the accommodation groove.

According to one embodiment, the light-shielding comb module may include: a first light-shielding comb module including a light-shielding comb part having a first length; and a second light-shielding comb module including a light-shielding comb part having a second length that is different from the first length.

According to one embodiment, the light-shielding comb module may include: a third light-shielding comb module including a light-shielding comb part having a first thickness; and a fourth light-shielding comb module including a light-shielding comb part having a second thickness that is different from the first thickness.

According to one embodiment, a first detachable attachment part detachably attached to the light-shielding comb module may be formed in the peripheral region of the body, and the light-shielding comb module may include a second detachable attachment part detachably attached to the peripheral region of the body.

To achieve the technical objects described above, according to the present invention, there is provided an IPL toilet bowl sterilizer.

According to one embodiment, the IPL toilet bowl sterilizer includes: at least one xenon lamp unit provided on one surface of an outer cover configured to rotate relative to an inner cover so as to sterilize the inner cover of a toilet bowl by emitting a xenon lamp light; and a control unit configured to control the xenon lamp unit to sterilize the inner cover of the toilet bowl.

According to one embodiment, the IPL toilet bowl sterilizer may further include a posture measurement sensor configured to provide angle information on an angle between the inner cover and the outer cover, and the control unit may be configured to sterilize the inner cover through the xenon lamp unit according to whether the angle provided by the posture measurement sensor is less than or equal to a predetermined angle.

According to one embodiment, the IPL toilet bowl sterilizer may further include a weight sensor configured to provide information on a weight applied to the inner cover, and the control unit may be configured to sterilize the inner cover through the xenon lamp unit according to whether the weight provided by the weight sensor is less than or equal to a predetermined weight.

According to one embodiment, the IPL toilet bowl sterilizer may further include a contamination level measurement sensor configured to provide information on a contamination level of the inner cover, and the control unit may be configured to sterilize the inner cover through the xenon lamp unit according to whether the contamination level provided by the contamination level measurement sensor is out of a predetermined criterion.

According to one embodiment, the IPL toilet bowl sterilizer may further include a driving unit configured to adjust a posture of the outer cover, and the control unit may be configured to control the xenon lamp unit to start sterilizing the inner cover from when the outer cover covers the inner cover at a predetermined angle until the outer cover is closed through the driving unit.

According to one embodiment, the IPL toilet bowl sterilizer may further include a temperature sensor configured to provide information on a temperature of the inner cover, and the control unit may be configured to provide information on whether the toilet bowl is available to a user according to the temperature provided by the temperature sensor immediately before the user uses the toilet bowl when the sterilization of the inner cover is completed through the xenon lamp unit.

According to one embodiment, the xenon lamp unit may include a first xenon lamp configured to emit a xenon lamp light toward one surface of the inner cover, and a second xenon lamp configured to emit a xenon lamp light toward the inner cover and a nozzle of a bidet of the toilet bowl, the control unit may be configured to operate in an inner cover sterilization mode for sterilizing the inner cover through the first xenon lamp and the second xenon lamp and in a nozzle sterilization mode for sterilizing the nozzle through the second xenon lamp, and a light intensity of the second xenon lamp in the nozzle sterilization mode may be greater than a light intensity of the second xenon lamp in the inner cover sterilization mode.

According to one embodiment, the IPL toilet bowl sterilizer may further include a spray unit provided on one side of the outer cover and configured to spray a sterilization liquid toward the inner cover.

Advantageous Effects

According to a first embodiment of the present invention, a portable IPL sterilizer may include: a body partitioned into a central region and a peripheral region surrounding at least a portion of the central region; a sterilization xenon lamp light source provided in the central region of the body; and a light-shielding comb part provided in the peripheral region of the body.

According to a second embodiment of the present invention, a portable IPL sterilizer may include: a body partitioned into a central region and a peripheral region surrounding at least a portion of the central region; a sterilization xenon lamp light source provided in the central region of the body; and at least one light-shielding comb module including a light-shielding comb part and detachably attached to the peripheral region of the body.

Accordingly, the portable IPL sterilizer can efficiently sterilize a sterilization target within a short time through the sterilization xenon lamp light source as compared with a conventional sterilizer using an ultraviolet light source.

In addition, according to an embodiment of the present invention, a reflective surface may be formed on one surface of the peripheral region of the body or on one surface of the light-shielding comb part, a comb body part may be formed on the light-shielding comb part, and at least one reflective member protruding by a predetermined length may be formed on one side of the peripheral region of the body or on one side of the light-shielding comb part.

Accordingly, the portable IPL sterilizer may reflect a light emitted from the xenon lamp light source toward the sterilization target through the reflective surface, the comb body part, and the reflective member, so that the sterilization target can be effectively sterilized.

In addition, according to the first embodiment of the present invention, the body may include an accommodation groove through which at least a portion of the light-shielding comb part is accommodated in the body in a longitudinal direction of the light-shielding comb part, and the portable IPL sterilizer may further include a comb length adjustment unit configured to adjust an accommodation length of the light-shielding comb part accommodated in the accommodation groove.

Accordingly, the portable IPL sterilizer may provide a light-shielding comb part adjusted to have a length corresponding to a length of scalp hair or body hair of the sterilization target through the comb length adjustment unit, so that combing that is optimized for the sterilization target can be provided.

In this case, the sterilization target may be a human or an animal.

In addition, according to the second embodiment of the present invention, the light-shielding comb module may include: a first light-shielding comb module including a light-shielding comb part having a first length; and a second light-shielding comb module including a light-shielding comb part having a second length that is different from the first length.

Accordingly, the portable IPL sterilizer may provide a light-shielding comb part having a length corresponding to a length or thickness of the scalp hair/body hair of the sterilization target through the first and second light-shielding comb modules, so that the combing that is optimized for the sterilization target can be provided.

Meanwhile, according to the second embodiment of the present invention, when the light-shielding comb module is separated from the body so as to solely use the body, the sterilization target can be sterilized by using the sterilization xenon lamp light source provided in the body.

In this case, the sterilization target may be a specific place, a predetermined space, or a specific object.

According to an embodiment of the present invention, an IPL toilet bowl sterilizer may include: at least one xenon lamp unit provided on one surface of an outer cover configured to rotate relative to an inner cover so as to sterilize the inner cover of a toilet bowl by emitting a xenon lamp light; and a control unit configured to control the xenon lamp unit to sterilize the inner cover of the toilet bowl.

Accordingly, the inner cover of the toilet bowl or a nozzle of a bidet can be sterilized within a short time by the xenon lamp light emitted from the xenon lamp unit.

Furthermore, since the inner cover of the toilet bowl or the nozzle of the bidet is sterilized by using the xenon lamp light emitted from the xenon lamp unit, the sterilization can be performed without making direct contact.

DESCRIPTION OF DRAWINGS

FIGS. 1 to 6 are views for describing a portable IPL sterilizer according to a first embodiment of the present invention.

FIGS. 7 to 19 are views for describing a portable IPL sterilizer according to a second embodiment of the present invention.

FIGS. 20 to 22 are views for describing an IPL toilet bowl sterilizer according to an embodiment of the present invention.

FIG. 23 is a flowchart for describing an inner cover sterilization mode according to the embodiment of the present invention.

FIG. 24 is a view for describing a step S100 according to the embodiment of the present invention.

FIG. 25 is a view for describing a step S200 according to the embodiment of the present invention.

FIGS. 26 to 29 are views for describing modified examples of the step S200 according to the embodiment of the present invention.

FIG. 30 is a flowchart for describing a nozzle sterilization mode according to the embodiment of the present invention.

FIGS. 31 and 32 are views for describing a step S300 according to the embodiment of the present invention.

FIGS. 33 and 34 are views for describing an experimental example of the present invention.

MODE FOR INVENTION

Hereinafter, exemplary embodiments of the present invention will be described in detail with reference to the accompanying drawings. However, the technical idea of the present invention is not limited to the embodiments described herein, but may be realized in different forms. The embodiments introduced herein are provided to sufficiently deliver the idea of the present invention to those skilled in the art so that the disclosed contents may become thorough and complete.

When it is mentioned in the present disclosure that one element is on another element, it means that one element may be directly formed on another element, or a third element may be interposed between one element and another element. Further, in the drawings, shapes and thicknesses of regions are exaggerated for effective description of the technical contents.

In addition, in various embodiments of the present disclosure, the terms such as first, second, and third are used to describe various elements, but the elements are not limited by the terms. The terms are used only to distinguish one element from another element. Therefore, an element mentioned as a first element in one embodiment may be mentioned as a second element in another embodiment. The embodiments described and illustrated herein include their complementary embodiments. Further, the term “and/or” used herein is used to include at least one of the elements enumerated before and after the term.

As used herein, expressions in a singular form include a meaning of a plural form unless the context clearly indicates otherwise. Further, the terms such as “including” and “having” are intended to designate the presence of features, numbers, steps, elements, or combinations thereof described in the present disclosure, and shall not be construed to preclude any possibility of the presence or addition of one or more other features, numbers, steps, elements, or combinations thereof. In addition, the term “connection” used herein is used to include both indirect and direct connections of a plurality of elements.

In addition, the term such as “ . . . unit”, “ . . . era”, or “module” described in the present disclosure refers to a unit for processing at least one function or operation, which may be implemented through hardware, software, or a combination of hardware and software.

Further, in the following description of the present invention, detailed descriptions of known functions or configurations incorporated herein will be omitted when they may make the gist of the present invention unnecessarily unclear.

According to an embodiment of the present invention, a portable IPL sterilizer 1000 may efficiently sterilize a sterilization target within a short time through a sterilization xenon lamp light source LS as compared with a conventional sterilizer using an ultraviolet light source.

In more detail, according to a first embodiment of the present invention, a portable IPL sterilizer 1000*a* in which a body 100 and a light-shielding comb part 200 are integrally formed may be provided.

The sterilization xenon lamp light source LS may be provided in a central region 120 of the body 100.

Accordingly, according to the first embodiment of the present invention, the portable IPL sterilizer 1000*a* may sterilize the sterilization target through the sterilization xenon lamp light source LS provided in the body 100 while combing the sterilization target through the light-shielding comb part 200.

In this case, the sterilization xenon lamp light source LS provided in the body 100 may sterilize a human, an object, an animal, and the like.

Meanwhile, according to a second embodiment of the present invention, a portable IPL sterilizer 1000*b* in which a body 100 and a light-shielding comb module 200M are separately provided may be provided.

A light-shielding comb part 200 may be provided on one surface of the light-shielding comb module 200M.

In more detail, a plurality of light-shielding comb modules 200M may be provided to provide light-shielding comb parts 200 having mutually different lengths or thicknesses according to a length or thickness of scalp hair/body hair of the sterilization target.

Accordingly, according to the second embodiment of the present invention, the portable IPL sterilizer 1000*b* may sterilize the sterilization target through the sterilization xenon lamp light source LS provided in the body 100 while combing the sterilization target through the light-shielding comb part 200 of the light-shielding comb module 200M selected according to the length or thickness of the scalp hair/body hair of the sterilization target.

Meanwhile, unlike the first embodiment, the portable IPL sterilizer 1000*b* according to the second embodiment may be configured as a separate type as described above, so that the body 100, which is not coupled to the light-shielding comb module 200M, may be solely used.

In this case, the sterilization xenon lamp light source LS may be provided in the central region 120 of the body 100. Accordingly, the body 100 may be used exclusively for sterilization purposes while not being coupled to the light-shielding comb module 200M.

In this case, the sterilization xenon lamp light source LS provided in the body 100 may sterilize a specific place, a predetermined space, a specific object, and the like. For example, the sterilization xenon lamp light source LS provided in the body 100 may sterilize a bathroom, a sink drainage hole, a toy, and the like.

Hereinafter, the portable IPL sterilizer according to the first embodiment of the present invention will be described with reference to the drawings.

FIGS. 1 to 6 are views for describing a portable IPL sterilizer according to a first embodiment of the present invention.

Referring to FIG. 1, according to the first embodiment of the present invention, the portable IPL sterilizer 1000*a* may include at least one of a body 100, a sterilization xenon lamp light source LS, a light-shielding comb part 200, and a handle 300.

According to one embodiment, the body 100 may be partitioned into a central region 120 and a peripheral region 140 surrounding at least a portion of the central region 120.

According to one embodiment, the sterilization xenon lamp light source LS may be provided in the central region 120 of the body. The sterilization xenon lamp light source LS may sterilize a sterilization target by emitting a strong short-pulsed light, that is, an intense pulsed light (IPL).

In more detail, the sterilization xenon lamp light source LS may emit the intense pulsed light (IPL) within a visible light wavelength band of 400 to 1200 nm.

When the light emitted from the sterilization xenon lamp light source LS reaches the sterilization target, energy of the emitted light may be absorbed on a surface of the sterilization target, so that a temperature of the surface of the sterilization target may be rapidly increased.

In other words, the temperature of the surface of the sterilization target to which the intense pulsed light (IPL) is emitted from the sterilization xenon lamp light source LS may be rapidly increased so that microorganisms present on the surface of the sterilization target may be killed.

According to a conventional sterilization method using an ultraviolet light source, a long time may be required to sterilize a sterilization target.

However, according to the embodiment of the present invention, the portable IPL sterilizer 1000*a* may include the sterilization xenon lamp light source LS, and the IPL may be emitted from the sterilization xenon lamp light source LS, so that the sterilization target may be efficiently sterilized within a short time as compared with the conventional sterilizer using the ultraviolet light source.

According to one embodiment, the light-shielding comb part 200 may be provided in the peripheral region 140 of the body. The light-shielding comb part 200 may comb the sterilization target.

In other words, according to the embodiment of the present invention, the portable IPL sterilizer 1000*a* may sterilize the sterilization target through the sterilization xenon lamp light source LS while combing the sterilization target through the light-shielding comb part 200.

In this case, the sterilization target may be understood as a concept including humans and animals. In particular, the animals may be understood as a concept including companion animals.

In other words, for example, the portable IPL sterilizer 1000*a* may sterilize the companion animal through the sterilization xenon lamp light source LS while combing hair of the companion animal through the light-shielding comb part 200.

In this case, for example, as shown in FIG. 1, the light-shielding comb part 200 may be configured such that a plurality of comb teeth are arranged in one row and one column along the peripheral region 140.

Alternatively, as another example, the light-shielding comb part 200 may be configured such that a plurality of comb teeth are arranged in a plurality of rows and a plurality of columns along the peripheral region 140. In this case, the arrangement of the comb teeth in the rows and the columns may be an arrangement according to a predetermined rule, or an irregular arrangement, that is, a random arrangement.

According to one embodiment, the handle 300 may be extend from one side of the body 100. Accordingly, the handle 300 may provide convenience according to a grip to a user who combs or sterilizes the sterilization target.

According to one embodiment, a control unit 320 may be provided on one side of the handle 300.

According to one embodiment, the control unit 320 may control the sterilization xenon lamp light source LS provided in the central region 120 of the body to emit a light.

To this end, the control unit 320 may be electrically connected to the sterilization xenon lamp light source LS. In addition, the control unit 320 may include a switch configured to turn on/off the sterilization xenon lamp light source LS.

In this case, the control unit 320 may be provided as, for example, a contact-type display such as a touch screen or as, as another example, a pressing button.

Hereinafter, each component of the portable IPL sterilizer 1000*a* according to the first embodiment of the present invention will be described in more detail with reference to FIGS. 2 to 6.

Referring to FIG. 2, a reflective surface 100RS may be formed on one surface of the central region 120 or the peripheral region 140 of the body. Accordingly, the reflective surface 100RS may reflect the light emitted from the sterilization xenon lamp light source LS so as to allow the light to reach the sterilization target.

To this end, the reflective surface 100RS may have a shape that allows the light emitted from the sterilization xenon lamp light source LS to be concentrated toward the sterilization target.

For example, as shown in FIG. 2, the reflective surface 100RS formed in the central region 120 may a shape that is concave toward the sterilization xenon lamp light source LS.

Accordingly, according to the embodiment of the present invention, the light emitted from the sterilization xenon lamp light source LS may easily reach the sterilization target so that the sterilization target may be effectively sterilized.

Referring to FIG. 3, the light-shielding comb part 200 may include at least one of a comb body part 202 and a thermochromic discoloration part 204.

According to one embodiment, the comb body part 202 may extend from the peripheral region 140 of the body by a predetermined length.

Accordingly, when the light is emitted from the sterilization xenon lamp light source LS provided in the central region 120 of the body, the comb body part 202 may reflect (RL2) the emitted light toward the sterilization target so that the emitted light may not escape to a region outside the body 100.

Accordingly, according to the embodiment of the present invention, the light emitted from the sterilization xenon lamp light source LS may easily reach the sterilization target so that the sterilization target may be effectively sterilized.

According to one embodiment, as shown in FIG. 3, the thermochromic discoloration part 204 may be provided at one end of the comb body part 202.

When the light is emitted from the sterilization xenon lamp light source LS provided in the central region 120 of the body, the thermochromic discoloration part 204 may be discolored by the emitted light.

In general, when a light is emitted from a xenon lamp, a high temperature that causes a burn or a fire may be accompanied.

However, according to the embodiment of the present invention, the portable IPL sterilizer 1000*a* may include the thermochromic discoloration part 204.

Accordingly, when the light is emitted from the sterilization xenon lamp light source LS, and a high temperature is accompanied as described above, a color of the thermochromic discoloration part 204 may be changed according to a temperature.

Therefore, a risk of a burn or a fire may be minimized through the changed color of the thermochromic discoloration part 204.

Referring to FIG. 4, at least one reflective member 100RC protruding by a predetermined length may be formed on one side of the peripheral region 140 of the body.

For example, as shown in FIG. 4, the reflective member 100RC may be formed on both sides of the peripheral region 140 of the body.

Accordingly, the reflective member 100RC may reflect the light emitted from the sterilization xenon lamp light source LS so as to minimize the light directly reaching an eye of the sterilization target, for example, a human or an animal.

According to one embodiment, a curved part 100CR may be formed on one side of the reflective member 100RC.

Accordingly, when the light emitted from the sterilization xenon lamp light source LS is reflected from the comb body part 202, the reflective member 100RC may reflect (RL3) the emitted light toward the sterilization target through the curved part 100CR.

In more detail, a situation in which the portable IPL sterilizer 1000*a* combs the sterilization target in a (−y)-direction as shown in FIG. 4 will be assumed.

In this case, the comb body part 202 may be convexly bent in the (−y)-direction.

In this case, when the light is emitted from the sterilization xenon lamp light source LS, the emitted light may be reflected from the comb body part 202 that is convexly bent in the (−y)-direction.

Accordingly, the light reflected from the comb body part 202 that is convexly bent in the (−y)-direction may be diffusely reflected without reaching the sterilization target.

However, according to the embodiment of the present invention, the portable IPL sterilizer 1000*a* may include the reflective member 100RC on which the curved part 100CR is formed, so that even when the comb body part 202 is convexly bent in the (−y)-direction, the light reflected from the comb body part 202 that is convexly bent in the (−y)-direction may be reflected (RL3) toward the sterilization target through the curved part 100CR.

Referring to FIG. 5, an accommodation groove 142 may be formed in the body 100.

According to one embodiment, the body 100 may accommodate at least a portion of the light-shielding comb part 200 through the accommodation groove 142.

In more detail, the body 100 may accommodate at least a portion of the light-shielding comb part 200 inside the body 100 through the accommodation groove 142 in a longitudinal direction (z-direction) of the light-shielding comb part 200.

In addition, referring to FIG. 5, a comb length adjustment unit 144 may be provided in the body 100.

According to one embodiment, the comb length adjustment unit 144 may adjust an accommodation length of the light-shielding comb part 200 accommodated in the accommodation groove 142.

Accordingly, a length of the light-shielding comb part 200 protruding from the body 100 may be adjusted.

For example, as shown in FIG. 5, the body 100 may accommodate at least a portion of the light-shielding comb part 200 through the accommodation groove 142, and a length of a light-shielding comb part 200A protruding outward of the body 100 may be L1.

Meanwhile, as shown in FIG. 6, the comb length adjustment unit 144 may be moved in the z-direction, so that at least a portion of the light-shielding comb part 200 accommodated in the accommodation groove 142 may protrude outside the body 100.

Accordingly, the length of the light-shielding comb part 200 protruding outward of the body 100 may be increased from a length of a first light-shielding comb part 200A having a length L1 shown in FIG. 5 to a length of a second light-shielding comb part 200B having a length L2 shown in FIG. 6.

Therefore, according to the embodiment of the present invention, the portable IPL sterilizer 1000*a* may be configured such that the length of the light-shielding comb part 200 is adjusted to be a length corresponding to a length of the scalp hair or the body hair of the sterilization target. Therefore, combing optimized for the sterilization target may be provided.

Hereinafter, the portable IPL sterilizer according to the second embodiment of the present invention will be described with reference to the drawings. Hereinafter, redundant descriptions corresponding to the portable IPL sterilizer according to the first embodiment of the present invention may be omitted.

FIGS. 7 to 19 are views for describing a portable IPL sterilizer according to a second embodiment of the present invention.

Referring to FIG. 7, according to the second embodiment of the present invention, the portable IPL sterilizer 1000*b* may include at least one of a body 100, a sterilization xenon lamp light source LS, a light-shielding comb module 200M, and a handle 300.

According to one embodiment, the body 100 may be partitioned into a first central region 120 and a first peripheral region 140 surrounding at least a portion of the first central region 120.

According to one embodiment, the sterilization xenon lamp light source LS may be provided in the first central region 120. As described above, the sterilization xenon lamp light source LS may sterilize a sterilization target by emitting an IPL.

In more detail, the sterilization xenon lamp light source LS may emit the intense pulsed light (IPL) within a visible light wavelength band of 400 to 1200 nm.

When the light emitted from the sterilization xenon lamp light source LS reaches the sterilization target, energy of the emitted light may be absorbed on a surface of the sterilization target, so that a temperature of the surface of the sterilization target may be rapidly increased.

In other words, the temperature of the surface of the sterilization target to which the intense pulsed light (IPL) is emitted from the sterilization xenon lamp light source LS may be rapidly increased so that microorganisms present on the surface of the sterilization target may be killed.

Accordingly, according to the embodiment of the present invention, as described above, the portable IPL sterilizer 1000*b* may efficiently sterilize the sterilization target within a short time through the sterilization xenon lamp light source LS as compared with the conventional sterilizer using the ultraviolet light source.

According to one embodiment, as shown in FIG. 8, a first detachable attachment part 100D may be formed in the first peripheral region 140.

The first detachable attachment part 100D may detachably attach the first peripheral region 140 to the light-shielding comb module 200M.

To this end, as shown in FIG. 9, a second detachable attachment part 200D detachably attached to the first peripheral region 140 may be formed in a second peripheral region 240 of the light-shielding comb module 200M.

In other words, the first peripheral region 140 and the second peripheral region 240 may be detachably attached to each other by detachably attaching the first detachable attachment part 100D to the second detachable attachment part 200D.

For example, as shown in FIG. 10, the first detachable attachment part 100D and the second detachable attachment part 200D may be detachably attached to each other by a male/female concavo-convex coupling scheme.

Alternatively, as another example, the first detachable attachment part 100D and the second detachable attachment part 200D may be detachably attached to each other by a magnetic coupling scheme (a coupling scheme by a magnetic force using a magnetic material) or a bonding medium coupling scheme (e.g., a coupling scheme by a non-woven tape).

In other words, while the portable IPL sterilizer 1000*a* according to the first embodiment of the present invention described above is configured such that the body 100 and the light-shielding comb part 200 are integrally formed, the portable IPL sterilizer 1000*b* according to the second embodiment of the present invention may be configured such that the body 100 and the light-shielding comb module 200M are separately provided.

Alternatively, according to another embodiment, as shown in FIG. 11, the body 100 and the light-shielding comb module 200M may be fitted and coupled to each other by at least one reflective member 100RC protruding from one side of the peripheral region 140 of the body by a predetermined length.

In this case, as shown in FIG. 11, a fitting groove 262 may be formed in the light-shielding comb module 200M in a region corresponding to the reflective member 100RC.

Accordingly, the reflective member 100RC and the fitting groove 262 may be fitted and coupled to each other.

Alternatively, according to another embodiment, as shown in FIG. 12, the light-shielding comb module 200M may have a shorter length than the body 100 in a y-direction.

In more detail, the light-shielding comb module 200M may have a shorter length than the body 100 in the y-direction so as to be detachably attached between at least one reflective member 100RC protruding from one side of the peripheral region 140 of the body 100 by a predetermined length.

In this case, a fitting part 162 may be provided on one side of the reflective member 100RC.

Meanwhile, a protrusion part 264 having a shape corresponding to the fitting part 162 may be provided in the light-shielding comb module 200M.

Accordingly, when the light-shielding comb module 200M is inserted between the reflective members 100RC, the fitting part 162 and the protrusion part 264 may be fitted and coupled to each other.

In an embodiment that will be described below, a description of a fitting and coupling structure may be omitted with reference to FIGS. 11 and 12. However, the embodiment of the fitting and coupling, which is described above with reference to FIGS. 11 and 12, may be identically applied below.

According to one embodiment, the light-shielding comb module 200M may be partitioned into a second central region 220 and a second peripheral region 240 surrounding at least a portion of the second central region 220.

As shown in FIG. 9, the second central region 220 may be an empty space surrounded by the second peripheral region 240.

According to one embodiment, lengths of the second central region 220 in an x-direction and the y-direction may be longer than lengths of the sterilization xenon lamp light source LS provided in the first central region 120 in the x-direction and the y-direction, respectively.

Accordingly, even when the light-shielding comb module 200M is coupled to the body 100, the xenon lamp light source LS of the body 100 may still be exposed toward an outside. In other words, the light emitted from the xenon lamp light source LS may be directed toward the sterilization target without being obstructed by the light-shielding comb module 200M.

According to one embodiment, the light-shielding comb part 200 may be provided on one side of the second peripheral region 240. The light-shielding comb part 200 may comb the sterilization target in the same manner as in the first embodiment of the present invention described above.

In other words, as described above, according to the embodiment of the present invention, the portable IPL sterilizer 1000*b* may sterilize the sterilization target by the sterilization xenon lamp light source LS while combing the sterilization target by the light-shielding comb part 200.

According to one embodiment, the handle 300 may be extend from one side of the body 100. Accordingly, the handle 300 may provide convenience according to a grip to a user who combs or sterilizes the sterilization target.

According to one embodiment, a control unit 320 may be provided on one side of the handle 300.

As described above, the control unit 320 may control the sterilization xenon lamp light source LS provided in the first central region 120 to emit a light.

Since the control unit 320 has been described above in the first embodiment of the present invention, redundant descriptions thereof will be omitted.

Hereinafter, each component of the portable IPL sterilizer 1000*b* according to the second embodiment of the present invention will be described in more detail with reference to FIGS. 13 to 19.

Referring to FIG. 13, a reflective surface 200RS may be formed on one surface of the second peripheral region 240 of the light-shielding comb module.

According to one embodiment, the reflective surface 200RS may reflect (RL1) the light emitted from the sterilization xenon lamp light source LS toward the sterilization target.

Accordingly, according to the embodiment of the present invention, when the first peripheral region 140 and the second peripheral region 240 are coupled to each other, and the light is emitted from the sterilization xenon lamp light source LS provided in the first central region 120, the light emitted from the sterilization xenon lamp light source LS may easily reach the sterilization target.

In this case, as described above, the reflective surface 100RS of the first central region 120 may have a shape that allows the light emitted from the sterilization xenon lamp light source LS to be concentrated toward the sterilization target.

For example, as shown in FIG. 13, the reflective surface 100RS formed in the central region 120 may have a shape that is concave toward the sterilization xenon lamp light source LS.

Accordingly, according to the embodiment of the present invention, the light emitted from the sterilization xenon lamp light source LS may easily reach the sterilization target so that the sterilization target may be effectively sterilized.

Referring to FIG. 14, the light-shielding comb part 200 may include at least one of a comb body part 202 and a thermochromic discoloration part 204.

According to one embodiment, the comb body part 202 may extend from the peripheral region 140 of the body by a predetermined length.

Accordingly, when the light is emitted from the sterilization xenon lamp light source LS provided in the first central region 120, the comb body part 202 may reflect (RL2) the emitted light toward the sterilization target so that the emitted light may not escape to a region outside the light-shielding comb module 200M.

Accordingly, according to the embodiment of the present invention, the light emitted from the sterilization xenon lamp light source LS may easily reach the sterilization target so that the sterilization target may be effectively sterilized.

According to one embodiment, as shown in FIG. 14, the thermochromic discoloration part 204 may be provided at one end of the comb body part 202.

The thermochromic discoloration part 204 may be discolored by the light emitted from the sterilization xenon lamp light source LS provided in the first central region 120.

As described above, when a light is emitted from a xenon lamp, a high temperature that causes a burn or a fire may be accompanied.

However, according to the embodiment of the present invention, the portable IPL sterilizer 1000*b* may include the thermochromic discoloration part 204, so that when the light is emitted from the sterilization xenon lamp light source LS, and a high temperature is accompanied, a color of the thermochromic discoloration part 204 may change according to a temperature.

Therefore, a risk of a burn or a fire may be minimized through the changed color of the thermochromic discoloration part 204.

Referring to FIG. 15, at least one reflective member 200RC protruding by a predetermined length may be formed on one side of the second peripheral region 240 of the light-shielding comb module.

According to one embodiment, a curved part 200CR may be formed on one side of the reflective member 200RC.

Accordingly, as described above, when the light emitted from the sterilization xenon lamp light source LS is reflected from the comb body part 202, the reflective member 200RC may reflect (RL3) the emitted light toward the sterilization target through the curved part 200CR.

In more detail, when the portable IPL sterilizer 1000*b* combs the sterilization target in the (−y)-direction as shown in FIG. 15, the comb body part 202 may be convexly bent in the (−y)-direction.

In this case, when the light is emitted from the sterilization xenon lamp light source LS, the emitted light may be reflected from the comb body part 202 that is convexly bent in the (−y)-direction.

Accordingly, according to the embodiment of the present invention, as described above, the portable IPL sterilizer 1000*b* may include the reflective member 200RC on which the curved part 200CR is formed, so that even when the comb body part 202 is convexly bent in the (−y)-direction, the light reflected from the comb body part 202 that is convexly bent in the (−y)-direction may be reflected (RL3) toward the sterilization target through the curved part 100CR, and thus diffused reflection may be minimized.

According to one embodiment, the light-shielding comb module 200M may include: a first light-shielding comb module 200M1 including a light-shielding comb part 200A having a first length L1 as shown in FIG. 16; and a second light-shielding comb module 200M2 including a light-shielding comb part 200B having a second length L2 that is different from the first length L1 as shown in FIG. 17.

Meanwhile, as described above, the first peripheral region 140 and the second peripheral region 240 may be detachably attached to each other by detachably attaching the first detachable attachment part 100D to the second detachable attachment part 200D.

Accordingly, the portable IPL sterilizer **1000*b* may selectively provide a light-shielding comb module 200M including a light-shielding comb part 200** having a length corresponding to the length of the scalp hair or the body hair of the sterilization target, so that combing optimized for the sterilization target may be provided.

In addition, the portable IPL sterilizer **1000*b* may provide a plurality of light-shielding comb modules 200M including light-shielding comb parts 200 having mutually different thicknesses, respectively. In other words, the light-shielding comb module 200M may be provided for each thickness of the light-shielding comb part 200. In this case, the light-shielding comb module 200**M may include: a third light-shielding comb module including a light-shielding comb part having a first thickness; and a fourth light-shielding comb module including a light-shielding comb part having a second thickness that is different from the first thickness.

Accordingly, the portable IPL sterilizer **1000*b* may selectively provide a light-shielding comb module 200**M according to the thickness of the scalp hair or the body hair of the sterilization target, so that combing optimized for the sterilization target may be provided.

In this case, as described above, for example, the light-shielding comb part 200 may be configured such that a plurality of comb teeth are arranged in one row and one column along the second peripheral region 240.

Alternatively, as another example, the light-shielding comb part 200 may be configured such that a plurality of comb teeth are arranged in a plurality of rows and a plurality of columns along the second peripheral region 240. In this case, the arrangement of the comb teeth in the rows and the columns may be an arrangement according to a predetermined rule, or an irregular arrangement, that is, a random arrangement.

Meanwhile, the portable IPL sterilizer **1000*b* according to the second embodiment of the present invention may be configured such that the body 100 may be solely used for sterilization purposes while not being coupled to the light-shielding comb module 200**M.

In more detail, referring to FIG. 18, as described above, the sterilization xenon lamp light source LS may be provided in the first central region 120, and The sterilization xenon lamp light source LS may sterilize the sterilization target by emitting the IPL.

In this case, the sterilization target may be understood as a concept that includes not only humans and animals, but also specific places, predetermined spaces, and specific objects, such as bathrooms, sink drainage holes, and toys.

In other words, when the combing is unnecessary, the portable IPL sterilizer **1000*b* may sterilize the sterilization target by using the sterilization xenon lamp light source LS provided in the first central region 120 while not being coupled to the light-shielding comb module 200**M.

In this case, as described above, a reflective surface 100RS may be formed on one surface of the first central region 120 or the first peripheral region 140.

As shown in FIG. 19, the reflective surface 100RS formed in the first central region 120 may have a shape that is concave toward the sterilization xenon lamp light source LS.

Accordingly, the portable IPL sterilizer **1000*b* may reflect (RL1) the light emitted from the sterilization xenon lamp light source LS toward the sterilization target through the reflective surface 100**RS.

Therefore, according to the embodiment of the present invention, the light emitted from the sterilization xenon lamp light source LS may easily reach the sterilization target so that the sterilization target may be effectively sterilized.

Furthermore, as described above with reference to FIGS. 11 and 12, at least one reflective member 100RC protruding by a predetermined length may be provided on one side of the peripheral region 140 of the body.

For example, as shown in FIG. 19, the reflective member 100RC may be formed on both sides of the peripheral region 140 of the body.

Accordingly, the reflective member 100RC may reflect (RL3) the light emitted from the sterilization xenon lamp light source LS so as to minimize the light directly reaching an eye of a human or an animal.

The first and second embodiments of the present invention described above may be variously utilized when the sterilization is necessary. For example, the first and second embodiments of the present invention may be utilized to sterilize a companion animal, a toy, a bathroom, a garment, and the like.

Hereinafter, an IPL toilet bowl sterilizer according to an embodiment of the present invention will be described with reference to the drawings.

FIGS. 20 to 22 are views for describing an IPL toilet bowl sterilizer according to an embodiment of the present invention.

Referring to FIGS. 20 to 22, an IPL toilet bowl sterilizer 2000 may include at least one of a power supply unit 1100, a xenon lamp unit 1200, a sensor unit 1300, a driving unit 1400, an output unit 1450, and a control unit 1500.

Hereinafter, each component will be described in detail.

The power supply unit 1100 may provide a current to drive at least one of the xenon lamp unit 1200, the sensor unit 1300, the driving unit 1400, the output unit 1450, and the control unit 1500.

To this end, the power supply unit 1100 may be provided independently on one side of a toilet bowl T. For example, the power supply unit 1100 may be configured such that a power plug provided independently on one side of the toilet bowl T is connected to an outlet, so that the power supply unit 1100 may provide the current to drive at least one of the xenon lamp unit 1200, the sensor unit 1300, the driving unit 1400, the output unit 1450, and the control unit 1500.

Meanwhile, unlike the above configuration, a power of a bidet of the toilet bowl may be utilized.

In other words, when the power of the bidet is utilized, a separate power may be omitted.

In this case, the bidet may be a device installed on the toilet bowl to perform cleaning after a user uses the toilet bowl. To this end, a nozzle NZ may be provided on one side of the bidet.

The xenon lamp unit 1200 may emit a xenon lamp light 1200L to sterilize an inner cover IC or a bidet nozzle NZ.

To this end, as shown in FIG. 20, at least one xenon lamp unit 1200 may be provided on one surface of an outer cover OC configured to rotate relative to the inner cover IC in a first direction ① or a second direction ② that is opposite to the first direction ①.

In this case, the one surface of the outer cover OC may be defined as a surface of the outer cover OC that faces a bowl of the toilet bowl.

In this case, as shown in FIG. 21, the xenon lamp unit 1200 may include at least one of a xenon lamp 1202, a reflective surface 1204, and quartz 1206.

According to one embodiment, the xenon lamp 1202 may emit a xenon lamp light 1200L. In more detail, the xenon lamp 1202 may sterilize the inner cover IC or the bidet nozzle NZ by emitting a strong short-pulsed light, that is, an intense pulsed light (IPL).

According to one embodiment, the reflective surface 1204 may be provided on one side of the xenon lamp 1202 to reflect the xenon lamp light 1200L emitted from the xenon lamp 1202 toward the inner cover IC or the bidet nozzle NZ.

According to one embodiment, the quartz 1206 may be provided on an opposite side of the xenon lamp 1202 to protect the xenon lamp 1202 from water or sewage in a use environment of the toilet bowl T, for example, in a situation in which the toilet bowl T is flushed. In other words, the quartz 1206 may minimize spattering or staining of the water or the sewage on the xenon lamp 1202.

According to one embodiment, the xenon lamp unit 1200 may include a first xenon lamp 1220 and a second xenon lamp 1240. The first xenon lamp 1220 may emit a xenon lamp light 1200L toward one surface of the inner cover IC.

To this end, similar to 1220*a* and 1220*b* shown in FIG. 20, at least one first xenon lamp 1220 may be provided on one surface of the outer cover OC to emit the xenon lamp light 1200L to the one surface of the inner cover IC.

In this case, the control unit 1500 may control the first xenon lamp 1220 to emit the xenon lamp light 1200L toward the one surface of the inner cover IC. The control of the first xenon lamp 1220 performed by the control unit 1500 will be described below in detail with reference to FIG. 25.

The second xenon lamp 1240 may emit a xenon lamp light 1200L toward the inner cover IC or the bidet nozzle NZ.

In more detail, the second xenon lamp 1240 may be operated in an inner cover sterilization mode in which the xenon lamp light 1200L is emitted toward the inner cover IC or in a nozzle sterilization mode in which the xenon lamp light 1200L is emitted toward the bidet nozzle NZ.

In this case, the second xenon lamp 1240 may emit the xenon lamp light 1200L at a higher intensity in the nozzle sterilization mode than in the inner cover sterilization mode. This will be described below in more detail with reference to FIGS. 31 and 32.

As shown in FIG. 20, at least one second xenon lamp 1240 may be provided on one side of the outer cover OC to emit the xenon lamp light to the inner cover IC or the bidet nozzle NZ.

In this case, the control unit 1500 may control the second xenon lamp 1240 to emit the xenon lamp light 1200L toward the inner cover IC or the bidet nozzle NZ. The control of the second xenon lamp 1240 performed by the control unit 1500 will be described below in detail with reference to FIGS. 31 and 32.

The sensor unit 1300 may provide predetermined information to the control unit 1500.

To this end, the sensor unit 1300 may be provided independently on one side of the toilet bowl T.

Meanwhile, unlike the above configuration, a sensor of the bidet of the toilet bowl may be utilized. In other words, when the sensor of the bidet is utilized, a separate sensor may be omitted.

In more detail, as shown in FIG. 22, the sensor unit 1300 may include at least one of a posture measurement sensor 1320, a weight sensor 1340, a contamination level measurement sensor 1360, and a temperature sensor 1380.

According to one embodiment, the posture measurement sensor 1320 may provide angle information on an angle between the inner cover IC and the outer cover OC to the control unit 1500.

According to one embodiment, the weight sensor 1340 may provide information on a weight applied to the inner cover IC to the control unit 1500.

According to one embodiment, the contamination level measurement sensor 1360 may provide information on a contamination level of the inner cover IC to the control unit 1500.

According to one embodiment, the temperature sensor 1380 may provide information on a temperature of the inner cover to the control unit 1500.

In this case, the control unit 1500 may control at least one of the xenon lamp unit 1200, the driving unit 1400, and the output unit 1450 according to predetermined information provided by the sensor unit 1300. This will be described below in detail.

The driving unit 1400 may adjust a posture of the outer cover OC.

In more detail, the driving unit 1400 may adjust the posture of the outer cover OC within a range from a covered posture in which the outer cover OC covers the inner cover IC to an open posture in which the inner cover IC is exposed.

In other words, the driving unit 1400 may be driven so that the outer cover OC covers the inner cover IC within a predetermined angle θ2. Accordingly, a sterilization area of the inner cover IC that is sterilized by the xenon lamp light 1200L emitted from the xenon lamp unit 1200 may be increased. This will be described below in detail with reference to FIG. 27.

As shown in FIG. 20, the driving unit 1400 may be provided on one side of a rotation shaft configured to rotate the outer cover OC relative to the inner cover IC in the first direction ① or the second direction ②.

According to one embodiment, the driving unit 1400 may include a stepping motor. Accordingly, a rotation shaft of the stepping motor may be rotated according to a pulse signal so that the outer cover OC may cover the inner cover IC within a predetermined angle θ2.

In this case, the control unit 1500 may control the driving unit 1400 so that the outer cover OC may cover the inner cover IC within the predetermined angle θ2. This will be described below in detail with reference to FIG. 27.

The output unit 1450 may provide a status message to the user.

To this end, according to one embodiment, the output unit 1450 may be provided on an opposite surface of the outer cover OC. In this case, the opposite surface of the outer cover OC may be defined as a surface of the outer cover OC that is exposed in the covered posture in which the outer cover OC covers the inner cover IC.

In other words, the output unit 1450 may be provided on the opposite surface of the outer cover OC to provide the status message to the user in the covered posture.

For example, when the inner cover IC is sterilized by the xenon lamp light 1200L emitted from the xenon lamp unit 1200 so that the temperature of the inner cover IC is high, the output unit 1450 may provide a status message of "The temperature of the inner cover is high." for the inner cover IC. This will be described below in detail with reference to FIG. 29.

Alternatively, according to one embodiment, the output unit 1450 may be provided on one side of the toilet bowl T.

A position in which the output unit 1450 is provided is not limited to the embodiments described above.

According to one embodiment, the output unit 1450 may be implemented as a display or an audio system.

Accordingly, the output unit 1450 may visually or audibly provide the status message to the user.

In this case, the control unit 1500 may control the output unit 1450 to provide the status message to the user. This will be described below in detail with reference to FIG. 29.

According to one embodiment, the IPL toilet bowl sterilizer 2000 may further include a button 1010 shown in FIG. 20.

The button 1010 may execute the sterilization of the inner cover IC in the inner cover sterilization mode that will be described below.

Alternatively, the button 1010 may execute the sterilization of the bidet nozzle NZ in the nozzle sterilization mode that will be described below.

To this end, as shown in FIG. 20, the button 1010 may be provided independently on one side of the toilet bowl T.

Meanwhile, unlike the above configuration, a button of the bidet of the toilet bowl may be utilized. In other words, when the button of the bidet is utilized, a separate button may be omitted.

In addition, according to one embodiment, the IPL toilet bowl sterilizer 2000 may further include a spray unit (not shown).

The spray unit may spray a sterilization liquid toward the inner cover IC.

To this end, the spray unit may be provided on one side of the outer cover OC.

The control unit 1500 may perform overall control of the IPL toilet bowl sterilizer 2000 according to one embodiment of the present invention.

In other words, the control unit 1500 may perform overall control of an operation of each component of the xenon lamp unit 1200, the sensor unit 1300, the driving unit 1400, and the output unit 1450.

To this end, the control unit 1500 may include a processor capable of performing a logical operation for controlling each component according to one embodiment. Meanwhile, unlike the above configuration, the control unit 1500 may be configured as a simple switch for controlling an on/off-state of the xenon lamp unit 1200.

Hereinafter, a method for controlling each component by the control unit 1500 will be described in detail.

FIG. 23 is a flowchart for describing an inner cover sterilization mode according to the embodiment of the present invention, FIG. 24 is a view for describing a step S100 according to the embodiment of the present invention, FIG. 25 is a view for describing a step S200 according to the embodiment of the present invention, FIGS. 26 to 29 are views for describing modified examples of the step S200 according to the embodiment of the present invention, FIG. 30 is a flowchart for describing a nozzle sterilization mode according to the embodiment of the present invention, FIGS. 31 and 32 are views for describing a step S300 according to the embodiment of the present invention, and FIGS. 33 and 34 are views for describing an experimental example of the present invention.

Hereinafter, the inner cover sterilization mode according to the present invention will be described.

Referring to FIG. 23, the inner cover sterilization mode may include determining whether sterilization is possible (or sterilization is necessary) (S100), or entering the inner cover sterilization mode (S200). Hereinafter, each step will be described in detail.

Step S100 In the step S100, the control unit 1500 may determine whether the sterilization is possible.

Hereinafter, the step S100 will be described in detail with reference to FIG. 24.

Referring to FIG. 24, the step S100 of determining whether the sterilization is possible may include at least one step among determining whether an outer cover OC is covered (S120), determining whether there is a user (S140), determining whether a contamination level is greater than or equal to a criterion (S160), and determining whether a button is pressed (S180).

When at least one step among the steps S120, S140, S160, and S180 is satisfied, the step S200 of entering the inner cover sterilization mode shown in FIG. 23 may be performed.

In other words, the steps S120, S140, S160, and S180 may correspond to steps of determining whether to start sterilization, and the steps may be variously combined. Hereinafter, each step will be described.

Step S120

In the step S120, the control unit 1500 may determine whether a state is a covered state in which the outer cover OC covers the inner cover IC.

This is to minimize the xenon lamp light 1200L, which is emitted from the xenon lamp unit 1200 to sterilize the inner cover IC, directly reaching an eye of the user of the toilet bowl T.

To this end, the control unit 1500 may receive the angle information on the angle between the inner cover IC and the outer cover OC from the posture measurement sensor 1320.

The control unit 1500 may determine the state as the covered state in which the outer cover OC covers the inner cover IC when the angle provided by the posture measurement sensor 1320 is less than or equal to a predetermined angle. For example, the control unit 1500 may determine the state as the covered state when the angle provided by the posture measurement sensor 1320 is 0 degree. A case where the angle of 0 degree is a criterion for determining the covered state is merely a simple example, so that the criterion may be set according to practice of those skilled in the art.

The control unit 1500 may determine that the sterilization is possible when determining the state as the covered state.

Therefore, the control unit 1500 may control to perform the entering of the inner cover sterilization mode that will be described below when determining the state as the covered state.

Accordingly, in the inner cover sterilization mode of the step that will be described below, the inner cover IC may be sterilized while minimizing the xenon lamp light 1200L reaching the eye of the user.

Meanwhile, when the angle provided by the posture measurement sensor 1320 exceeds the predetermined angle, the control unit 1500 may determine the state as an open state in which the outer cover OC rotates relative to the inner cover IC so as to be open. For example, the control unit 1500 may determine the state as the open state when the angle provided by the posture measurement sensor 1320 exceeds 0 degree.

The control unit 1500 may determine that the sterilization is impossible when determining the state as the open state.

Therefore, the control unit 1500 may not control to perform the entering of the inner cover sterilization mode that will be described below when determining the state as the open state.

Accordingly, according to the embodiment of the present invention, the xenon lamp light 1200L may not be emitted in the open state so as to minimize the xenon lamp light 1200L directly reaching the eye of the user of the toilet bowl T.

Meanwhile, the control unit 1500 may continuously receive the angle information on the angle between the inner cover IC and the outer cover OC from the posture measurement sensor 1320.

Thereafter, the control unit 1500 may determine the state as the covered state so as to determine that the sterilization is possible when determining that the angle provided from the posture measurement sensor 1320 is less than or equal to the predetermined angle.

Therefore, the control unit 1500 may enter the step S200 that will be described below.

Meanwhile, when the step S120 is not satisfied, the control unit 1500 may control the state to satisfy the step S120.

For example, the control unit 1500 may control the driving unit 1400 to allow the state to be the covered state when determining the state as the open state immediately after the user uses the toilet bowl T.

Accordingly, when the state is the open state, the outer cover OC may rotate relative to the inner cover IC to automatically cover the inner cover IC.

Thereafter, as described above through the step S120, the control unit 1500 may determine whether the outer cover OC is covered.

The control unit 1500 may determine that the sterilization is possible when determining the state as the covered state.

Therefore, the control unit 1500 may control to perform the entering of the inner cover sterilization mode that will be described below when determining the state as the covered state.

Step S140

In the step S140, the control unit 1500 may determine whether there is a user seated on the toilet bowl T.

This is to minimize a user risk that may occur when the sterilization starts while the user is using the toilet bowl.

To this end, the control unit 1500 may receive the information on the weight applied to the inner cover IC from the weight sensor 1340.

The control unit 1500 may determine a state as an unused state in which the user does not use the toilet bowl T when the weight provided by the weight sensor 1340 is less than or equal to a predetermined weight. For example, the control unit 1500 may determine the state as the unused state when the weight provided by the weight sensor 1340 is 0 kg. A case where the weight of 0 kg is a criterion for determining the unused state is merely a simple example, so that the criterion may be set according to practice of those skilled in the art.

The control unit 1500 may determine that the sterilization is possible when determining the state as the unused state.

Therefore, the control unit 1500 may control to perform the entering of the inner cover sterilization mode that will be described below when determining the state as the unused state.

Accordingly, in the inner cover sterilization mode of the step that will be described below, the inner cover IC may be sterilized while minimizing the user risk that may occur when the sterilization starts while the user is using the toilet bowl.

Meanwhile, the control unit 1500 may determine the state as a used state in which the user is using the toilet bowl T when the weight provided by the weight sensor 1340 exceeds the predetermined weight. For example, the control unit 1500 may determine the state as the used state when the weight provided by the weight sensor 1340 exceeds 0 kg.

The control unit 1500 may determine that the sterilization is impossible when determining the state as the used state.

Therefore, the control unit 1500 may not control to perform the entering of the inner cover sterilization mode that will be described below when determining the state as the used state.

Accordingly, according to the embodiment of the present invention, the user risk that may occur when the sterilization starts while the user is using the toilet bowl may be minimized.

Meanwhile, the control unit 1500 may continuously receive the information on the weight applied to the inner cover IC from the weight sensor 1340.

Thereafter, the control unit 1500 may determine the state as the unused state so as to determine that the sterilization is possible when determining that the weight provided from the weight sensor 1340 is less than or equal to the predetermined weight.

Therefore, the control unit 1500 may enter the step S200 that will be described below.

Step S160

In the step S160, the control unit 1500 may determine whether the contamination level of the inner cover IC is greater than or equal to the criterion.

This is to save energy by minimizing unnecessary emission of the xenon lamp light 1200L from the xenon lamp unit 1200 when the contamination level of the inner cover IC is less than the criterion, while the xenon lamp light 1200L is emitted from the xenon lamp unit 1200 to automatically sterilize the inner cover IC when the contamination level of the inner cover IC is greater than or equal to the criterion.

To this end, the control unit 1500 may receive the information on the contamination level of the inner cover IC from the contamination level measurement sensor 1360.

The control unit 1500 may determine the state as a contaminated state in which the inner cover IC is contaminated when the contamination level of the inner cover IC provided by the contamination level measurement sensor 1360 is greater than or equal to a predetermined criterion. For example, the control unit 1500 may determine the state as the contaminated state when the contamination level of the inner cover IC provided by the contamination level measurement sensor 1360 is 200 relative light units (RLU). A case where the contamination level of 200 RLU is a criterion for determining the contaminated state is merely a simple example, so that the criterion may be set according to practice of those skilled in the art.

The control unit 1500 may determine that the sterilization is necessary when determining the state as the contaminated state.

Therefore, the control unit 1500 may control to perform the entering of the inner cover sterilization mode that will be described below when determining the state as the contaminated state.

Accordingly, in the inner cover sterilization mode of the step that will be described below, the inner cover IC may be sterilized.

Meanwhile, the control unit 1500 may determine the state as a non-contaminated state in which the inner cover IC is not contaminated when the contamination level of the inner cover IC provided by the contamination level measurement sensor 1360 is less than the predetermined criterion. For example, the control unit 1500 may determine the state as the non-contaminated state when the contamination level of the inner cover IC provided by the contamination level measurement sensor 1360 is less than 200 RLU.

The control unit 1500 may determine that the sterilization is unnecessary when determining the state as the non-contaminated state.

Therefore, the control unit 1500 may not control to perform the entering of the inner cover sterilization mode that will be described below when determining the state as the non-contaminated state.

Accordingly, according to the embodiment of the present invention, the xenon lamp light 1200L may not be emitted in the non-contaminated state so that the energy may be saved by minimizing the unnecessary emission of the xenon lamp light 1200L.

Meanwhile, the control unit 1500 may continuously receive the information on the contamination level of the inner cover IC from the contamination level measurement sensor 1360.

Thereafter, the control unit 1500 may determine the state as the contaminated state so as to determine that the sterilization is necessary when determining that the contamination level of the inner cover IC provided from the contamination level measurement sensor 1360 is greater than or equal to the predetermined criterion.

Therefore, the control unit 1500 may enter the step S200 that will be described below.

Step S180

In the step S180, the control unit 1500 may determine whether the button 1010 for executing the sterilization of the inner cover IC is pressed. In this case, as described above with reference to FIG. 20, the button 1010 may be an inner cover sterilization mode button for executing the sterilization of the inner cover IC.

This is to receive sterilization intention information on whether the user desires to sterilize the inner cover IC immediately before the user uses the toilet bowl T.

To this end, the control unit 1500 may receive the information on an intention of the user to sterilize the inner cover IC from the button 1010.

As described above, as shown in FIG. 20, the button 1010 may be provided independently on one side of the toilet bowl T.

Meanwhile, unlike the above configuration, a button of the bidet of the toilet bowl may be utilized. In other words, when the button of the bidet is utilized, a separate button may be omitted.

When the button 1010 is pressed, the control unit 1500 may determine that the user has provided a sterilization intention in which the user desires to sterilize the inner cover IC.

Accordingly, the control unit 1500 may determine that the sterilization is necessary.

Therefore, the control unit 1500 may control to perform the entering of the inner cover sterilization mode that will be described below when determining that the user has provided the sterilization intention.

Accordingly, in the inner cover sterilization mode of the step that will be described below, the inner cover IC may be sterilized when the user desires to sterilize the inner cover IC immediately before the user uses the toilet bowl T.

Meanwhile, when the button 1010 is not pressed, the control unit 1500 may determine that the user does not desire to sterilize the inner cover IC immediately before the user uses the toilet bowl T. Accordingly, the control unit 1500 may determine that the sterilization is unnecessary.

Therefore, the control unit 1500 may not control to perform the entering of the inner cover sterilization mode that will be described below when determining that the sterilization is unnecessary.

Accordingly, according to the embodiment of the present invention, the xenon lamp light 1200L may not be emitted in the used state so as to minimize a burn risk of the user of the toilet bowl T caused by the xenon lamp light 1200L.

Accordingly, the inner cover IC may be non-sterilized when the user does not desire to sterilize the inner cover IC immediately before the user uses the toilet bowl T.

Meanwhile, the control unit 1500 may continuously receive information on whether the button 1010 is pressed.

Thereafter, the control unit 1500 may determine that the user has provided the sterilization intention to sterilize the inner cover IC immediately before the user uses the toilet bowl T so as to determine that the sterilization is necessary when the button 1010 is pressed.

Therefore, the control unit 1500 may enter the step S200 that will be described below.

As described above, in the step S100 described above, the control unit 1500 may determine that the sterilization is possible (or the sterilization is necessary) when at least one step among the steps S120 to S180 is satisfied. In this case, the term "satisfy" means that it is determined as being able to proceed to the step S200. For example, "Yes" of the step S120, "No" of the step S140, "Yes" of the step S160, and "Yes" of the step S180 in FIG. 24 may correspond to the satisfaction.

The control unit 1500 may perform the step S200 when at least one step among the steps S120 to S180 is satisfied. In this case, when the steps S120 and S140 are satisfied, the control unit 1500 may start the sterilization of the step S200. In other words, the steps S120 and S140 may be essential conditions before the step S200.

As a specific example, when the steps S120 and S140 are satisfied, the step S200 may be performed. In other words, the sterilization of the step S200 may be started when the outer cover is closed, and there is no user.

Alternatively, as another example, when the steps S120, S140, and S160 are satisfied, the step S200 may be performed. In other words, the sterilization of the step S200 may be started when the outer cover is closed, there is no user, and the contamination level is greater than or equal to the predetermined level.

Alternatively, as another example, when the steps S120, S140, and S180 are satisfied, the step S200 may be performed. In other words, the sterilization of the step S200 may be stated when the outer cover is closed, there is no user, and the button is pressed.

Alternatively, as another example, when the steps S120, S140, S160, and S180 are satisfied, the step S200 may be performed. In other words, the sterilization of step S200 may be stated when the outer cover is closed, there is no user, the contamination level is greater than or equal to the predetermined level, and the button is pressed.

Therefore, the control unit 1500 may control to enter the step S200.

Meanwhile, according to the embodiment of the present invention, the control unit 1500 may control the driving unit 1400 to allow the state to be the covered state when determining that the step S120 is not satisfied, that is, when determining that the outer cover is opened. Accordingly, preparation to satisfy the step S120 may be performed.

Hereinafter, the step S200 will be described with reference to the drawings.

Step S200

In the step S200, the control unit 1500 may enter the inner cover sterilization mode.

To this end, the control unit 1500 may control the xenon lamp unit 1200 to sterilize the inner cover IC by emitting the xenon lamp light.

In more detail, as shown in FIG. 25, the control unit 1500 may control the first xenon lamps 1220*a* and 1220*b* and the second xenon lamp 1240 to emit a xenon lamp light 1200L1. Accordingly, the inner cover IC may be sterilized.

Hereinafter, a modified example of the step S200 will be described with reference to FIGS. 26 to 29. Hereinafter, each step will be described.

Step S220

According to a modified example, the sterilization through the xenon lamp light may be started not only from a state in which the outer cover OC completely covers the inner cover IC, but also from a state in which the outer cover OC covers the inner cover IC at a predetermined angle or less, so that the sterilization area of the inner cover IC may be maximized.

In detail, in a step S220, as shown in FIG. 26, the control unit 1500 may determine whether the outer cover OC covers the inner cover IC within a predetermined angle θ2.

As described above, this is to maximize the sterilization area of the inner cover IC.

To this end, the control unit 1500 may receive the angle information on the angle between the inner cover IC and the outer cover OC from the posture measurement sensor 1320.

The control unit 1500 may determine that the outer cover OC covers the inner cover IC within the predetermined angle θ2 when the angle provided by the posture measurement sensor 1320 is within the predetermined angle θ2.

In this case, the predetermined angle θ2 may be understood as a concept including an angle at which the xenon lamp light is not emitted to the eye of the user, for example, a case where the angle between the inner cover IC and the outer cover OC is 10 degrees.

The control unit 1500 may control the xenon lamp unit 1200 to start sterilizing the inner cover IC when determining that the covering is performed within the predetermined angle.

In more detail, when the step S120 has been satisfied, that is, when the outer cover OC has closed the inner cover IC, the control unit 1500 may control the driving unit 1400 so as to rotate the outer cover OC relative to the inner cover IC in the second direction of FIG. 27 (the direction ② of FIG. 27). Accordingly, the outer cover OC may have a posture of covering the inner cover IC within the predetermined angle θ2, that is, a predetermined open posture in the covered state.

Thereafter, as shown in FIG. 27, the control unit 1500 may control the first xenon lamps 1220*a* and 1220*b* and the second xenon lamp 1240 to emit a xenon lamp light 1200L1*a*. The control unit 1500 may control the xenon lamp so that the sterilization may be continuously performed while the outer cover OC is closed in the first direction (the direction ① of FIG. 27) through the driving unit 1400. For example, the control unit 1500 may control the sterilization of the inner cover IC to be continuously performed from a case where the outer cover OC covers the inner cover IC within the predetermined angle θ2 as shown in FIG. 27 until the covered state of FIG. 25, that is, until the angle between the inner cover IC and the outer cover OC reaches 0 degree.

Accordingly, the outer cover OC may cover the inner cover IC within the predetermined angle θ2 so that the xenon lamp light 1200L1*a* emitted from the first xenon lamps 1220*a* and 1220*b* and the second xenon lamp 1240 provided on one surface of the outer cover OC may reach the inner cover IC over a larger area than the xenon lamp light 1200L1 emitted in the covered state as shown in FIG. 25.

Accordingly, the sterilization area of the inner cover IC may be maximized.

Step S240

According to the modified example, the user may be warned immediately before the user uses the toilet bowl T in a situation where the sterilization of the inner cover IC is completed so that the temperature of the inner cover IC is high, so that the burn risk of the user may be minimized. To this end, the present step may be performed between the step S100 and the step S200 of FIG. 23. Alternatively, the present step may be performed when the user is expected to use the toilet bowl T during the sterilization according to the step S200.

In detail, in the step S240, as shown in FIG. 28, the control unit 1500 may determine whether the temperature of the inner cover IC is greater than or equal to a predetermined temperature.

This is to minimize the burn risk of the user as described above.

To this end, the control unit 1500 may receive the information on the temperature of the inner cover IC from the temperature sensor 1380.

The control unit 1500 may determine that the temperature of the inner cover IC is a high temperature when the temperature of the inner cover IC provided from the temperature sensor 1380 is greater than or equal to the predetermined temperature. For example, the control unit 1500 may determine that the temperature is the high temperature when the temperature provided by the temperature sensor 1380 is 40° C. A case where the temperature of 40° C. is a criterion for determining a high temperature is merely a simple example, so that the criterion may be set according to practice of those skilled in the art.

In this case, the high temperature may be understood as a concept including a temperature that is sufficient for the user to get burned.

According to one embodiment, when the control unit 1500 determines that the temperature of the inner cover IC is high, the control unit 1500 may control the driving unit 1400 to be in a locking state in which the outer cover OC is fixed while covering the inner cover IC as shown in FIG. 29.

In addition, the control unit 1500 may control the driving unit 1400 to maintain the locking state when determining that the temperature of the inner cover IC is not decreased to a temperature at which the user does not get burned.

Accordingly, the outer cover OC may not rotate relative to the inner cover IC in the second direction θ of FIG. 29.

Accordingly, the outer cover OC may not rotate so as to be open relative to the inner cover IC having a temperature that is increased by the xenon lamp light 1200L, so that the burn risk of the user of the toilet bowl T may be minimized.

Alternatively, according to another embodiment, the control unit 1500 may control the output unit 1450 to provide a status message to the user through the output unit 1450 when determining that the temperature of the inner cover IC is greater than or equal to the predetermined temperature.

For example, as shown in FIG. 29, the control unit 1500 may control the output unit 1450 to provide a status message of "The temperature of the inner cover is high." when the temperature of the inner cover IC is greater than or equal to the predetermined temperature.

Alternatively, as another example, as shown in FIG. 29, the control unit 1500 may control the output unit 1450 to provide a status message informing of the locking state.

In other words, the control unit 1500 may provide information on whether the toilet bowl T is available to the user according to the temperature provided by the temperature sensor 1380 immediately before the user uses the toilet bowl T when the sterilization of the inner cover IC is completed through the xenon lamp unit 1200.

Accordingly, the burn risk of the user of the toilet bowl T caused by the inner cover IC having the temperature that is increased by the xenon lamp light 1200L may be minimized.

Meanwhile, the control unit 1500 may continuously receive the information on the temperature of the inner cover IC from the temperature sensor 1380.

The control unit 1500 may determine that the temperature of the inner cover IC is a low temperature when the temperature of the inner cover IC provided from the temperature sensor 1380 is less than the predetermined temperature. For example, the control unit 1500 may determine that the temperature is the low temperature when the temperature provided by the temperature sensor 1380 is less than 40° C.

In this case, unlike the concept of the high temperature described above, the low temperature may be understood as a concept including a temperature that does not cause the user to get burned.

According to one embodiment, the control unit 1500 may control the driving unit 1400 to release the locking state shown in FIG. 29 when determining that the temperature of the inner cover IC is low.

Accordingly, the outer cover OC may rotate relative to the inner cover IC in the second direction ② of FIG. 29. Therefore, the user may use the toilet bowl T.

Alternatively, according to another embodiment, the control unit 1500 may provide a status message to the user through the output unit 1450 when determining that the temperature of the inner cover IC is less than the predetermined temperature.

For example, the control unit 1500 may control the output unit 1450 to provide a status message informing of a use status of the toilet bowl T. For example, the control unit 1500 may control the output unit 1450 to provide a status message of "Available." when the temperature of the inner cover IC is less than the predetermined temperature, and the driving unit 1400 is in an unlocking state.

Accordingly, the user may use the toilet bowl T within a temperature range in which the burn risk is minimized.

The embodiment of the locking described above and the embodiment of providing the status message described above may be variously combined according to an operation of the user or a predetermined program.

In addition, the control unit 1500 may provide the information on whether the toilet bowl T is available to the user according to the temperature provided by the temperature sensor 1380 not only immediately before the user uses the toilet bowl T, but also while the inner cover IC is sterilized through the xenon lamp unit 1200. For example, the control unit 1500 may control the driving unit 1400 to be in the locking state and control the output unit 1450 to provide a status message of "Sterilizing." or "Unavailable." while the inner cover IC is sterilized through the xenon lamp unit 1200.

Hereinafter, the nozzle sterilization mode according to the present invention will be described.

According to the embodiment of the present invention, the bidet nozzle NZ may be sterilized separately from the inner cover IC in the nozzle sterilization mode.

In this case, the bidet nozzle NZ may refer to a nozzle provided on one side of the bidet to spray water in order to perform cleaning after the user uses the toilet bowl. Bacteria may easily proliferate in the bidet nozzle NZ due to a humid environment caused by the spray of the water.

Accordingly, according to the present invention, a method for sterilizing the bidet nozzle NZ that will be described with reference to FIGS. 30 to 32 as well as the method for sterilizing the inner cover IC that is described above with reference to FIGS. 23 to 29 may be provided.

Referring to FIG. 30, the nozzle sterilization mode may include determining whether sterilization is possible (or sterilization is necessary) (S100), or entering the nozzle sterilization mode (S300). Hereinafter, each step will be described in detail.

Step S100

In the step S100, the control unit 1500 may determine whether the sterilization is possible.

Referring again to FIG. 24, the step S100 of determining whether the sterilization is possible may include at least one step among determining whether an outer cover OC is covered (S120), determining whether there is a user (S140), determining whether a contamination level is greater than or equal to a criterion (S160), and determining whether a button is pressed (S180).

Since detailed descriptions of the above configuration are the same as the descriptions set forth above, the detailed descriptions thereof will be omitted.

Meanwhile, the step S160 of the nozzle sterilization mode may be the same as the step S160 of the inner cover sterilization mode described above except that a target for which the criterion of the contamination level is determined is changed to the bidet nozzle NZ from the inner cover IC of the inner cover sterilization mode. In other words, in the nozzle sterilization mode, the bidet nozzle NZ may be sterilized according to whether the contamination level of the bidet nozzle NZ is greater than or equal to the criterion. Therefore, redundant descriptions of the nozzle sterilization mode corresponding to the inner cover sterilization mode will be omitted.

Meanwhile, the step S180 of the nozzle sterilization mode may be the same as the step S180 of the inner cover sterilization mode described above except that the inner cover sterilization mode button of the inner cover sterilization mode is changed into a nozzle sterilization mode button for executing the sterilization of the bidet nozzle NZ. Therefore, redundant descriptions of the nozzle sterilization mode corresponding to the inner cover sterilization mode will be omitted.

In addition, redundant descriptions of even steps that will be described below corresponding to the above descriptions may be omitted.

As described above, in the step S100 described above, the control unit 1500 may determine that the sterilization is possible (or the sterilization is necessary) when at least one step among the steps S120 to S180 is satisfied.

Therefore, the control unit 1500 may control to enter the step S300.

Hereinafter, the step S300 will be described with reference to the drawings.

Step S300

In the step S300, the control unit 1500 may enter the nozzle sterilization mode.

To this end, the control unit 1500 may control the xenon lamp unit 1200 to sterilize the bidet nozzle NZ by emitting the xenon lamp light 1200L.

In more detail, as shown in FIG. 31, the control unit 1500 may control the second xenon lamp 1240 to emit a xenon lamp light 1200L2. Accordingly, the bidet nozzle NZ may be sterilized.

In this case, the control unit 1500 may control driving of the second xenon lamp 1240. In other words, in the nozzle sterilization mode, the control unit 1500 may drive only the second xenon lamp 1240 to control the second xenon lamp 1240 to emit the xenon lamp light 1200L2.

In addition, as shown in FIG. 32, the control unit 1500 may control the second xenon lamp 1240 to emit the xenon lamp light 1200L2 at a higher intensity than in the inner cover sterilization mode (1200L1).

This may be because a separation distance between the second xenon lamp 1240, which is a sterilization light source provided in the nozzle sterilization mode, and the bidet nozzle NZ, which is a sterilization target, is greater than a separation distance between the first xenon lamp 1220 and the second xenon lamp 1240, which are sterilization light sources provided in the inner cover sterilization mode, and the inner cover IC, which is a sterilization target.

Accordingly, the xenon lamp light 1200L2 emitted from the second xenon lamp 1240 may reach the bidet nozzle NZ. Therefore, the bidet nozzle NZ may be sterilized by the xenon lamp light 1200L2 emitted from the second xenon lamp 1240.

On the contrary, when the xenon lamp light is not emitted at a higher intensity in the nozzle sterilization mode than in the inner cover sterilization mode, the emitted xenon lamp light may not reach the bidet nozzle. Therefore, the bidet nozzle may not be sterilized by the xenon lamp light emitted in the nozzle sterilization mode.

However, according to the embodiment of the present invention, the xenon lamp light 1200L2 may be emitted at a higher intensity in the nozzle sterilization mode than in the inner cover sterilization mode (1200L1). Therefore, the xenon lamp light 1200L2 emitted from the second xenon lamp 1240 may reach the bidet nozzle NZ. Therefore, the bidet nozzle NZ may be sterilized by the xenon lamp light 1200L2 emitted from the second xenon lamp 1240.

The inner cover sterilization mode described with reference to FIGS. 23 to 25, a first modified example described with reference to FIGS. 26 and 27, a second modified example described with reference to FIGS. 28 and 29, and the nozzle sterilization mode described with reference to FIGS. 30 to 32 may be variously combined according to an operation of the user or a predetermined program.

Hereinafter, an experimental example of the present invention will be described.

FIGS. 33 and 34 are views for describing an experimental example of the present invention.

*Escherichia coli* were cultured by using an aqueous solution medium, the xenon lamp light 1200L was emitted through the xenon lamp unit 1200 according to the present invention, and sterilization results were observed.

Referring to FIGS. 33 and 34, a greatest sterilization effect was exhibited when one pulse of the xenon lamp light 1200L is emitted at a voltage of 550 V through the xenon lamp unit 1200 according to the present invention.

In other words, according to the embodiment of the present invention, the xenon lamp light 1200L may be emitted from the xenon lamp unit 1200 in a short time corresponding to a unit of several seconds, so that the sterilization may be simply performed without making direct contact with the toilet bowl.

Since the sterilization results shown in FIGS. 33 and 34 have been provided for illustrative purposes, a greater sterilization effect may be obtained by applying a higher voltage Volt or increasing a number of pulses # Pulse while emitting the xenon lamp light 1200L of the xenon lamp unit 1200 according to the present invention.

Although the exemplary embodiments of the present invention have been described in detail above, the scope of the present invention is not limited to a specific embodiment, and shall be interpreted by the appended claims. In addition, it is to be understood by those of ordinary skill in the art that various changes and modifications can be made without departing from the scope of the present invention.

The invention claimed is:

1. An IPL toilet bowl sterilizer comprising:

at least one xenon lamp unit provided on one surface of an outer cover configured to rotate relative to an inner cover so as to sterilize the inner cover of a toilet bowl by emitting a xenon lamp light;

a control unit configured to control the at least one xenon lamp unit to sterilize the inner cover of the toilet bowl;

a driving unit configured to adjust a posture of the outer cover; and a temperature sensor configured to provide information on a temperature of the inner cover, wherein the control unit is configured to:

start sterilization of the inner cover by controlling the at least one xenon lamp unit only in a section from a time point when the outer cover covers the inner cover at a predetermined angle until a time point when the outer cover is completely closed, during a process in which the outer cover moves through the driving unit; and after the sterilization of the inner cover is completed and immediately before a user uses the toilet bowl, control the driving unit to a locking state or provide information on unavailability of the toilet bowl to the user when the temperature of the inner cover measured by the temperature sensor is greater than or equal to a preset temperature.

2. The IPL toilet bowl sterilizer of claim 1, further comprising a posture measurement sensor configured to provide angle information on an angle between the inner cover and the outer cover, wherein the control unit is configured to sterilize the inner cover through the at least one xenon lamp unit according to whether the angle provided by the posture measurement sensor is less than or equal to a predetermined angle.

3. The IPL toilet bowl sterilizer of claim 1, further comprising a weight sensor configured to provide information on a weight applied to the inner cover, wherein the control unit is configured to sterilize the inner cover through the at least one xenon lamp unit according to whether the weight provided by the weight sensor is less than or equal to a predetermined weight.

4. The IPL toilet bowl sterilizer of claim 1, further comprising a contamination level measurement sensor configured to provide information on a contamination level of the inner cover, wherein the control unit is configured to sterilize the inner cover through the at least one xenon lamp unit according to whether the contamination level provided by the contamination level measurement sensor is out of a predetermined criterion.

5. The IPL toilet bowl sterilizer of claim 1, wherein the at least one xenon lamp unit includes a first xenon lamp configured to emit a xenon lamp light toward one surface of the inner cover, and a second xenon lamp configured to emit a xenon lamp light toward the inner cover and a nozzle of a bidet of the toilet bowl, the control unit is configured to operate in an inner cover sterilization mode for sterilizing the inner cover through the first xenon lamp and the second xenon lamp and in a nozzle sterilization mode for sterilizing the nozzle through the second xenon lamp, and a light intensity of the second xenon lamp in the nozzle sterilization mode is greater than a light intensity of the second xenon lamp in the inner cover sterilization mode.

6. The IPL toilet bowl sterilizer of claim 1, further comprising a spray unit provided on one side of the outer cover and configured to spray a sterilization liquid toward the inner cover.

* * * * *